US006221352B1

(12) United States Patent
Howell et al.

(10) Patent No.: US 6,221,352 B1
(45) Date of Patent: *Apr. 24, 2001

(54) METHOD OF PREVENTING THE PROLIFERATION OF Vβ14 OR Vβ17-EXPRESSING T CELLS

(75) Inventors: Mark D. Howell, Fort Collins, CO (US); Steven W. Brostoff, Carlsbad; Dennis J. Carlo, Rancho Santa Fe, both of CA (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/471,209

(22) Filed: Jun. 6, 1995

Related U.S. Application Data

(62) Division of application No. 08/276,776, filed on Jul. 18, 1994, which is a continuation of application No. 07/813,867, filed on Dec. 24, 1991, now abandoned, which is a continuation-in-part of application No. 07/644,611, filed on Jan. 22, 1991, now abandoned, which is a continuation-in-part of application No. 07/530,229, filed on May 30, 1990, now abandoned, which is a continuation-in-part of application No. 07/382,085, filed on Jul. 18, 1999, now abandoned, and application No. 07/382,086, filed on Jul. 18, 1989, now abandoned, which is a continuation-in-part of application No. 07/326,314, filed on Mar. 21, 1989, now abandoned.

(51) Int. Cl.[7] .................. A61K 39/395; A61K 39/40; A61K 39/42; C07K 16/00

(52) U.S. Cl. .................... 424/139.1; 424/144.1; 424/154.1; 424/183.1; 424/1.49; 424/578; 530/387.1

(58) Field of Search .............. 530/387.1; 424/144.1, 424/154.1, 183.1, 578, 139.1, 1.49

(56) References Cited

U.S. PATENT DOCUMENTS

| | | |
|---|---|---|
| 4,444,744 * | 4/1984 | Goldenberg . |
| 4,886,743 | 12/1989 | Hood et al. . |
| 5,189,147 * | 2/1993 | Saito . |
| 5,194,425 * | 3/1993 | Sharma et al. . |
| 5,223,426 * | 6/1993 | Skibbons et al. . |
| 5,336,598 * | 8/1994 | Kotzin et al. . |

FOREIGN PATENT DOCUMENTS

| | | |
|---|---|---|
| 0 340 109 A3 | 4/1989 | (EP) . |
| WO 86/06413 | 11/1986 | (WO) . |
| WO 90/11294 | 10/1990 | (WO) . |
| WO 91/01133 | 2/1991 | (WO) . |
| WO 91/15225 | 10/1991 | (WO) . |
| WO 92/12996 | 8/1992 | (WO) . |
| 92/11159 | 1/1993 | (WO) . |

OTHER PUBLICATIONS

Abe et al., *Proc. Natl. Acad. Sci. USA* 89:4066–4070 (1992).

Acha–Orbea et al., "Limited heterogeneity of T cell receptors from lymphocytes mediatinng autoimmune encephalomyelitis allows specific immune intervention." *Cell* 54:263–273 (1988).

Ben–Nun et al., "Vaccination against autoimmune encephalomyelitis with T–lymphocite line cells reactive against myelin basic protein." *Nature* 292:60–61 (1981).

Biddison et al., "The germline repertoire of T–cell receptor beta–chain genes in patients with multiple sclerosis." *Res. Immunol.* 140:212–215 (1989).

Brostoff et al., "T Cell receptors, immunoregulation, and autoimmunity." *Clinical Immunology and Immunopathology* 62:1–7 (1992).

Brostoff et al., *Immunol. Ser.* 59:203–218 (1993).

Burns et al., Both rat and mouse T cell receptors specific for the encephalitogenic determinant of myelin basic protein use similar V α and V β chain genes even though the major histocompatibility complex of encephalitogenic determinants being recognized are different. *J. Exp. Med.* 169:27–39 (1989).

Choi et al. "Interaction of *Staphylococcus aureus* toxin "superantigens" with human T cells." *Proc. Natl. Acad. Sci. USA* 86:8941–8945 (1989).

Chluba et al., "T cell receptor β chain usage in myelin basic protein–specific rat T lymphocytes." *Eur. J. Immunol.* 19:279–284 (1989).

(List continued on next page.)

*Primary Examiner*—Patrick J. Nolan
*Assistant Examiner*—Gerald R. Ewoldt
(74) *Attorney, Agent, or Firm*—Campbell & Flores LLP

(57) ABSTRACT

The present invention provides vaccines and a means of vaccinating a vertebrate so as to prevent or control specific T cell mediated pathologies, including autoimmune diseases and the unregulated replication of T cells. The vaccine is composed of a T cell receptor (TCR) or a fragment thereof corresponding to a TCR present on the surface of T cells mediating the pathology. The vaccine fragment can be a peptide corresponding to sequences of TCRs characteristic of the T cells mediating said pathology. Such a peptide can bind to conventional antigens completed to MHC antigen presenting cells or to superantigens. Means of determining appropriate amino acid sequences for such vaccines are also provided. The vaccine is administered to the vertebrate in a manner that induces an immune response directed against the TCR of T cells mediating the pathology. This immune response down regulates or deletes the pathogenic T cells, thus ablating the disease pathogenesis. The invention additionally provides specific β-chain variable regions of T cell receptors, designated Vβ3, Vβ4, Vβ12, Vβ14 and Vβ17, which are associated with the pathogenesis of autoimmune diseases, such as rheumatoid arthritis (RA) and multiple sclerosis (MS). Also provided are means to detect, prevent and treat RA and MS. Methods of administering DNA or RNA encoding the polypeptides useful as vaccines of the present invention into the tissue cells of an individual is also provided.

4 Claims, 3 Drawing Sheets

OTHER PUBLICATIONS

Choi et al., *Proc. Natl. Acad. Sci. USA* 88:8357 (1991).
Clark et al., *Ann. Neurol.* 31:587–592 (1992).
Cohen and Weiner, *Immunol. Today* 9:332–335 (1988).
Edouard et al., *Eur. J. Immunol.* 23:727–733 (1993).
Esch et al., *Crit. Rev. Immunol.* 11(5):249–264 (19).
Gaur et al., *Science* 259:91–93 (1991).
Gregorian et al., *FASEB J.* 6:A1685 (1992).
Grunewald et al., *Eur. J. Immunol.* 22:129–135 (1992).
Grunewald et al., *Scand. J. Immunol.* 34:161–168 (1992).
Howell et al., *Proc. Natl. Acad. Sci. USA* 88:10921–10925 (1991).
Howell et al., "Vaccination against experimental allergic encephalomyelitis with T cell receptor peptides." *Science* 246:668–670 (1989).
Infante et al., *J. Immunol.* 148:3385–3390 (1992).
Janeway, C., "Self superantigens?" *Cell* 63:659–661 (1990).
Kawano et al., *Cancer Eye Res.* 10:789–795 (1991).
Kimura et al., Sequences and repertoire of the human T cell receptor α and β chain variable region genes in thymocytes. *Eur. J. Immunol.* 17:375–383 (1987).
Lahesmaa et al., *J. Immunol.* 150:4125–4135 (1993).
Lee et al., *Ann. Neurol.* 29:33–40 (1991).
Lider et al., "Anti–idiotypic network induced by T cell vaccination against experimental autoimmune encephalomyelitis." *Science* 239:181–183 (1988).
Lohse et al., *Science* 244:820–822 (1988).
Marrack and Kappler, "The staphylococcal enterotoxins and their relatives." *Science* 248:705–711 (1990).
Offner et al., "Lymphocyte vaccination against experimental autoimmune encephalomyelitis: evaluation of vaccination protocols." *J. Neuroimmunol.* 21:13–22 (1989).
Owhashi and Heber–Katz, "Protection from experimental allergic encephalomyelitis conferred by a monoclonal antibody directed against a shared idiotype on rat T cell receptors specific for myelin basic protein." *J. Exp. Med.* 168:2153–2164 (1988).
Paliard et al., *Science* 253:325–329 (1991).
Patten et al., "Structure, expression and divergence of T–cell receptor β–chain variable regions." *Nature* 312:40–46 (1984).
Posnett et al., *J. Clin. Invest.* 85:1770–1776 (1990).
Pullen et al., "Identification of the region of T cell receptor B chain that interacts with the self–superantigen Mis–1$^a$." *Cell* 61:1365–1374 (1990).
Ross et al., "Antibodies to synthetic peptides corresponding to variable–region first–framework segments of T cell receptors." *Immunol. Res.* 8:81–97 (1989).
Schluter et al., "Antibodies to synthetic joining segment peptide of the T–cell receptor β–chain: serological cross--reaction between products of T–cell receptor genes, antigen binding T–cell receptors and immunoglobulins." *Chem. Abstracts* 105(1):464, abstract No. 4767q (1986).

Sedgwick, J. "Long–term depletion of CD8 T cells in vivo in the rat: no observed role for CD8 (cytotoxic/suppressor) cells in the immunoregulation of experimental allergic encephalomyelitis." *Eur. J. Immunol.* 18:495–502 (1988).
Sellins et al., *J. Immunol.* 149:2323–2327 (1992).
Smith et al., *Blood* 81:1521–1526 (1993).
Sun et al., "Suppression of experimentally induced autoimmune encephalomyelitis by cytolytic T–T cell interacitons." *Nature* 332:843–845 (1988).
Urban et al., "Restricted use of T cell receptor V genes in murine autoimmune encephalomyelitis raises possibilities for antibody therapy." *Cell* 54:577–592 (1988).
Vandenbark et al., "Immunization with a synthetic T–cell receptor V–region peptide protects against experimental autoimmun encephalomyelitis." *Nature* 341:541–544 (1989).
White et al., "The Vβ–specific superantigen staphylococcal enterotooxin B: stimulation of mature T cells and clonal deletion in enonatal mice." *Cell* 56:27–35 (1989).
Wucherpfennig et al., *Science* 248:1016–1019 (1990).
Wucherpfennig et al., "Shared human T cell receptor Vβ usage to immunodominant regions of myelin basic pprotein." *Science* 248:1016–1019 (1990).
Yanagi et al., "A human T cell–specific cDNA clone encodes a protein having extensive homology to immunoglobulin chains." *Nature* 308:145–149 (1984).
Zamvil et al., "Predominant expression of a T cell receptor $V_\beta$ gene subfamily in autoimmune encephalomyelitis," *J. Exp. Med.* 167:1586–1596 (1988).
Davies et al. in Fundamental Immunology 4th Edition. Ep W. Paul. Lippincoh–Raven Philadelphia 1999 p. 355–356.*
Padulp et al. J. Immunol. 146:879, 1991.*
Hom et al. Immunological Investigations 22 257, 1993.*
Vandenbark et al. J. of Neuroscience 43:393, 1996.*
Brostoff, S. in Monoclonal Antibodies and Peptide Therapy in Autoimmune Disoages. Ed. J.F Bach.*
Yoshina et al. J. Exp. Med 175: 907–915, 1992.*
Maeda et al. Arthritis and Rheumatism 37: 406–413, 1994.*
Acha–Orbea et al 1988 54: 263.*
Urban et al 1988 Cell 54: 577.*
Hapler et al 1996 Immunol. Today 17: 152.*
Waith et al 1989 Cell: 57 709.*
Jansen et al 1989 Cancer Imm. & Immtherum 28:225.*
Owhashi et al Dec. 1988 J. Exp. Med 168:2153–.*
Kuppler et al. 1987 Cell. 49: 263.*

* cited by examiner

```
                                                                CDR4
                                          CDR2                ┌─────────────────────────┐
           CDR1                    ┌──────────────────┐       │EKKERFSLILESASTNQTSMYLCASS
┌────────────────────────┐         │DPGLGLRLIYFSYDVKMKEKG│DIPEGYSVSR│EKRNFPLILESPSNQTSLYFCASS
│FLAVGLVDKVTQSSRYLV│KRTGEKVFLECVQDMDHENMFWYRQ│DPGLGLRQIYYSMNVEVTDKG│DVPEGYKVSR│KEKESFPLTVTSAQKNPTAFYLCASS
MGPQLLGYVVLQ│LLGAGPLEAQVTQNPRYLI│TVTGKKLTVTCSQNMNHEYMSWYRQ│DPGQGLRLIYYSQIVNDFQKG│DIAEGYSVSR│
MSNQVLCCVVLQFLGANTVDGGITQSPKYLFRKEGQNVTLSCEQNLNHDAMYWYRQ└──────────────────┘       └─────────────────────────┘
└────────────────────────┘ vβ3
vβ14
vβ17
```

FIG. 1

| Vβcons | 5' | G  AC        CAAA<br>T  TC TGGTA     CA<br>T  TT      TCGT | 3' |
|---|---|---|---|
| Vβ17 | 5' | TCACAGATAGTAAATGACTTTCAG | 3' |
| Vβ8 | 5' | TCTCCACTCTGAAGATCC | 3' |
| Vβ12 | 5' | GATTTCCTCCTCACTCTG | 3' |
| 5'Cβ | 5' | CAAGCTGTTCCCACCCGA | 3' |
| Cβext | 5' | CCAGAAGGTGGCCGAGAC | 3' |
| Cβint | 5' | GCGGCTGCTCAGGCAGTA | 3' |
| Cβseq | 5' | CGACCTCGGGTGGGAACA | 3' |

METHOD OF PREVENTING THE PROLIFERATION OF Vβ14 OR Vβ17-EXPRESSING T CELLS

This application is a divisional of application Ser. No. 08/276,776, filed Jul. 18, 1994, allowed Jan. 3, 2000 which is a continuation of application U.S. Ser. No. 07/813,867 filed Dec. 24, 1991, now abandoned which is a continuation-in-part of U.S. Ser. No. 07/644,611 filed Jan. 22, 1991, now abandoned which is a continuation-in-part of U.S. Ser. No. 07/530,229 filed May 30, 1990, now abandoned which is a continuation-in-part of U.S. Ser. Nos. 07/382,085 and 07/382,086 both filed Jul. 18, 1989, both now abandoned which are continuations-in-part of U.S. Ser. No. 07/326,314 filed Mar. 21, 1989. Now abandoned the contents of all such related applications are incorporated herein by reference in their entirety.

BACKGROUND OF THE INVENTION

This invention relates to the immune system and, more specifically, to methods of modifying pathological immune responses.

Higher organisms are characterized by an immune system which protects them against invasion by potentially deleterious substances or microorganisms. When a substance, termed an antigen, enters the body, and is recognized as foreign, the immune system mounts both an antibody-mediated response and a cell-mediated response. Cells of the immune system termed B lymphocytes, or B cells, produce antibodies that specifically recognize and bind to the foreign substance. Other lymphocytes termed T lymphocytes, or T cells, both effect and regulate the cell-mediated response resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies.

Numerous diseases are believed to result from autoimmune mechanisms. Prominent among these are rheumatoid arthritis, systemic lupus erythematosus, multiple sclerosis, Type I diabetes, myasthenia gravis and pemphigus vulgaris. Autoimmune diseases affect millions of individuals worldwide and the cost of these diseases, in terms of actual treatment expenditures and lost productivity, is measured in billions of dollars annually. At present, there are no known effective treatments for such autoimmune pathologies. Usually, only the symptoms can be treated, while the disease continues to progress, often resulting in severe debilitation or death.

In other instances, lymphocytes replicate inappropriately and without control. Such replication results in a cancerous condition known as a lymphoma. Where the unregulated lymphocytes are of the T cell type, the tumors are termed T cell lymphomas. As with other malignancies, T cell lymphomas are difficult to treat effectively.

Thus, a long-felt need exists for an effective means of curing or ameliorating T cell mediated pathologies. Such a treatment should ideally control the inappropriate T cell response, rather than merely reducing the symptoms. The present invention satisfies this need and provides related advantages as well.

SUMMARY OF THE INVENTION

The present invention provides vaccines and a means of vaccinating a vertebrate so as to prevent or control specific T cell mediated pathologies. The vaccine is composed of a substantially pure T cell receptor (TCR) or an immunogenic fragment thereof corresponding to a TCR present on the surface of T cells mediating the pathology. The vaccine fragment can be a peptide corresponding to sequences of TCRs characteristic of the T cells mediating said pathology.

The invention additionally provides specific β-chain variable regions and their immunogenic segments, and in particular three T cell receptors, designated Vβ3, Vβ14 and Vβ17, which are associated with the pathogenesis of autoimmune diseases, for example rheumatoid arthritis (RA) and multiple sclerosis (MS). Additional VDJ junctional (CDR3) regions associated with other autoimmune diseases are also provided. The present invention further relates to means for detecting, preventing and treating RA, MS and other autoimmune diseases.

The invention further provides methods of preventing or treating T cell mediated pathologies, including RA and MS, by gene therapy. In these methods, pure DNA or RNA encoding for a TCR, an immunogenic fragment thereof or an anti-idiotype antibody having an internal image of a TCR or an immunogenic fragment is administered to an individual. Vectors containing the DNA or RNA and compositions containing such vectors are also provided for use in these methods.

BRIEF DESCRIPTION OF THE FIRGURES

FIG. 1 shows the variable region sequences of Vβ3, Vβ14 and Vβ17 (SEQ ID NOS:75, 8 and 7, respectively). The boxed segments depict the CDR1, CDR2 and CDR4 hypervariable regions of each Vβ chain. The sequences between the CDR2 and CDR4 regions represent an overlap between these two hypervariable regions.

DETAILED DESCRIPTION OF THE INVENTION

Figures 2A, 2B:
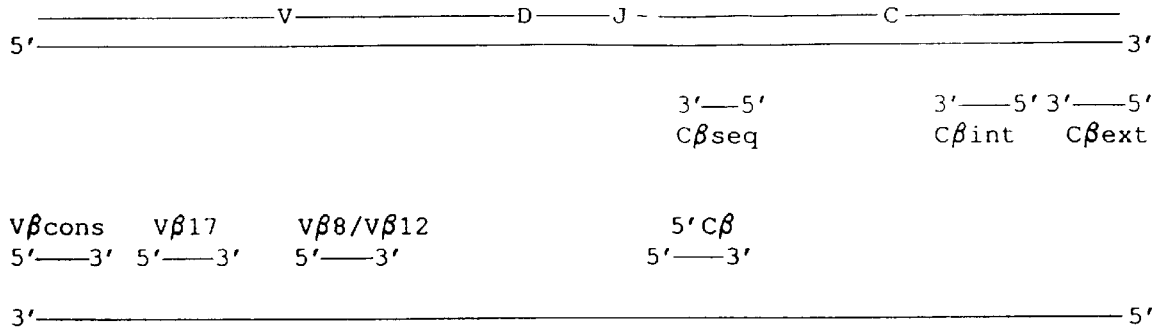
FIG. 2(A) shows the location of primers used in polymerase chain reaction amplification of T cell receptor β-chain genes, and 2(B) shows primer sequences used in polymerase chain reaction (SEQ ID NOS:47 through 55, respectively).

The invention generally relates to vaccines and their use for preventing, ameliorating or treating T cell-mediated pathologies, such as autoimmune diseases and T cell lymphomas. Vaccination provides a specific and sustained treatment which avoids problems associated with other potential avenues of therapy.

As used herein, the term "T cell-mediated pathology" refers to any condition in which an inappropriate T cell response is a component of the pathology. The term is intended to encompass both T cell mediated autoimmune diseases and diseases resulting from unregulated clonal T cell replication. In addition, the term is intended to include both diseases directly mediated by T cells and those, such as myasthenia gravis, which are characterized primarily by damage resulting from antibody binding, and also diseases in which an inappropriate T cell response contributes to the production of those antibodies.

As used herein, "substantially the amino acid sequence," or "substantially the sequence" when referring to an amino acid sequence, means the described sequence or other sequences having any additions, deletions or substitutions that do not substantially effect the ability of the sequence to elicit an immune response against the desired T cell receptor sequence. Such sequences commonly have many other sequences adjacent to the described sequence. A portion or segment of the described immunizing sequence can be used so long as it is sufficiently characteristic of the desired T cell receptor or fragment thereof to cause an effective immune response against desired T cell receptors, but not against undesired T cell receptors. Such variations in the sequence can easily be made, for example by synthesizing an alternative sequence. The alternate sequence can then be tested, for example by immunizing a vertebrate, to determine its effectiveness.

As used herein, the term "fragment" means an immunogenically effective subset of the amino acid sequence that comprises a TCR. The term is intended to include such fragments in conjunction with or combined with additional sequences or moieties, as for example where the peptide is coupled to other amino acid sequences or to a carrier. The terms "fragment" and "peptide" can, therefore, be used interchangeably since a peptide will be the most common fragment of the T cell receptor. Each fragment of the invention can have an altered sequence, as described above for the term "substantially the sequence."

Reference herein to a "fragment," "portion" or "segment" of a T cell receptor does not mean that the composition must be derived from intact T cell receptors. Such "fragments," portions" or "segments" can be produced by various means well-known to those skilled in the art, such as, for example, manual or automatic peptide synthesis, various methods of cloning or enzymatic treatment of a whole TCR.

As used herein when referring to the relationship between peptide fragments of the invention and sequences of TCRs, "corresponding to" means that the peptide fragment has an amino acid sequence which is sufficiently homologous to a TCR sequence or fragment thereof to stimulate an effective regulatory response in the individual. The sequence, however, need not be identical to the TCR sequence as shown, for instance, in Examples II and III.

By "immunogenically effective" is meant an amount of the T cell receptor or fragment thereof which is effectively elicits an immune response to prevent or treat a T cell mediated pathology or an unregulated T cell clonal replication in an individual. Such amounts will vary between species and individuals depending on many factors for which one skilled in the art can determine.

As used herein, "binding partner" means a compound which is reactive with a TCR. Generally, this compound will be a Major Histocompatibility Antigen (MHC) but can be any compound capable of directly or indirectly stimulating T cell activation or proliferation when bound to the TCR. Such compounds can also, for example, be a superantigen that binds to a superantigen binding site on the TCR.

As used herein, "individual" means any vertebrate, including humans, capable of having a T cell mediated pathology or unregulated clonal T cell replication and is used interchangeably with "vertebrate."

As used herein, "ligand" means any molecule that reacts with another molecule to form a complex.

As used herein, "selectively binds" means that a molecule binds to one type of molecule or related group of molecules, but not substantially to other types of molecules. In relation to V$\beta$s, "selective binding" indicates binding to TCRs or fragments thereof containing a specific V$\beta$ without substantial cross-reactivity with other TCRs that lack the specific V$\beta$.

The immune system is the primary biological defense of the host (self) against potentially pernicious agents (nonself). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

The principal manifestations of an antigen-specific immune response are humoral immunity (antibody mediated) and cellular immunity (cell mediated). Each of these immunological mechanisms are initiated through the activation of helper (CD4+) T Cells. These CD4+ T cells in turn stimulate B cells, primed for antibody synthesis by antigen binding, to proliferate and secrete antibody. This secreted antibody binds to the antigen and facilitates its destruction by other immune mechanisms. Similarly, CD4+ T cells provide stimulatory signals to cytotoxic (CD8+) T cells that recognize and destroy cellular targets (for example, virus infected cells of the host). Thus, the activation of CD4+ T cells is the proximal event in the stimulation of an immune response. Therefore, elaboration of the mechanisms underlying antigen specific activation of CD4+ T cells is crucial in any attempt to selectively modify immunological function.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, joining (J) region gene segments and constant (C) region gene segments. Beta and delta chains contain an additional element termed the diversity (D) gene segment. Since D segments and elements are found in only some of the TCR genetic loci, and polypeptides, further references herein to D segments and elements will be in parentheses to indicate the inclusion of these regions only in the appropriate TCR chains. Thus, V(D)J refers either to VDJ sequences of chains which have a D region or refers to VJ sequences of chains lacking D regions.

With respect to the beta chain of the variable region referred to as a V$\beta$, the nomenclature used herein to identify specific V$\beta$s follows that of Kimura et al., *Eur. J. Immuno.* 17:375–383 (1987), with the exception that the V$\beta$14 herein corresponds to V$\beta$3.3 of Kimura et al.

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of binding partners to which an organism may be exposed. However, a particular T cell will have only one TCR molecule and that TCR molecule, to a large degree if not singly, determines the specificity of that T cell for its binding partner.

Animal models have contributed significantly to the understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells having specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific not only for the same antigen (MBP), but usually also for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were found. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

An alternative mechanism for T cell activation has been suggested in which endogenous and exogenous superantigens have been shown to mediate T-cell stimulation as described, for example, in White et al, *Cell* 56:27–35 (1989) and Janeway, *Cell* 63:659–661 (1990).

As used herein, "superantigens" means antigens or fragments thereof that bind preferentially to T cells at specific sites on the β chain of a TCR and stimulate T cells at very high frequency rate. Such superantigens can be endogenous or exogenous. "Frequency" refers to the proportion of T cells responding to antigens and ranges from about $\frac{1}{5}$ to $\frac{1}{100}$ in response to superantigens. Thus, superantigens are distinguishable from conventional antigens, which have a much lower T cell response frequency rate ranging from about $\frac{1}{10^4}$ to $\frac{1}{10^6}$. Superantigens activate T cells by binding to specific Vβs. The superantigen binding sites of various TCRs have been distinguished from the conventional hypervariable regions (CDRs) of TCRs. These CDRs represent the regions of TCRs thought to be responsible for binding conventional antigens that are complexed to MHC.

The present invention provides an effective method of immunotherapy for T cell mediated pathologies, including autoimmune diseases, which avoids many of the problems associated with previously suggested methods of treatment. By vaccinating, rather than passively administering heterologous antibodies, the host's own immune system is mobilized to suppress the autoaggressive T cells. Thus, the suppression is persistent and may involve any or all immunological mechanisms in effecting that suppression. This multi-faceted response is more effective than the uni-dimensional suppression achieved by passive administration of monoclonal antibodies or ex vivo-derived regulatory T cell clones which requires a highly individualized therapeutic approach because of MHC non-identity among humans in order to avoid graft versus host reactions. The methods of the present invention are also more effective than vaccination with attenuated disease-inducing T cells that lack specificity for the protective antigen on the surface of a particular T cell as well as the variable induction of immunity to that antigen. In addition, vaccination with attenuated T cells is plagued by the same labor intensiveness and need for individualized therapies as noted above for ex vivo derived regulatory T cell clones.

As they relate to autoimmune disease, the vaccine peptides of the present invention comprise TCRs or immunogenic fragments thereof from specific T cells that mediate autoimmune diseases. The vaccines can be whole TCRs substantially purified from T cell clones, individual T cell receptor chains (for example, alpha, beta, etc.) or portions of such chains, either alone or in combination. The vaccine can be homogenous, for example, a single peptide, or can be composed of more than one type of peptide, each of which corresponds to a different portion of the TCR. Further, these peptides can be from different TCRs that contribute to the T cell mediated pathology. These vaccine peptides can be of variable length so long as they can elicit a regulatory response. Preferably, such peptides are between about 5–100 amino acids in length, and more preferably between about 6–25 amino acids in length.

In a specific embodiment, the immunizing peptide can have the amino acid sequence of a β-chain VDJ region when the subject has MS or RA. Any immunogenic portion of these peptides can be effective, particularly a portion having substantially the sequence SGDQGGNE (SEQ ID No. 1) or CAIGSNTE (SEQ ID No. 2) of Vβ4 and Vβ12, respectively, for MS; or, substantially the sequence ASSLGGAVSYN (SEQ ID No. 3), ASSLGGEETQYF (SEQ ID No. 4), ASSLGGFETQYF (SEQ ID No. 5) or ASSLGGTEAFF (SEQ ID No. 6) for RA. Thus, amino acid substitutions can be made which do not destroy the immunogenicity of the peptide. Additionally, this peptide can be linked to a carrier to further increase its immunogenicity. Alternatively, whole T cell receptors or TCR fragments that include these sequences can be used to vaccinate directly.

In a further specific embodiment, T cell receptors, whole T cells or fragments of TCRs that contain Vβ17, Vβ14 or Vβ3 can be used to immunize an individual having a T cell mediated pathology to treat or prevent the disease. In a specific embodiment, rheumatoid arthritis can be so treated. The immune response generated in the individual can neutralize or kill T cells having Vβ17, Vβ14 or Vβ3 and, thus, prevent or treat the deleterious effects of such Vβ-bearing T cells. Moreover, to the extent that Vβ17, Vβ14 or Vβ3 is common to T cell receptors on pathogenic T cells mediating other autoimmune diseases or autoimmune diseases in general, such vaccines can also be effective in ameliorating such other autoimmune diseases.

As used herein, "Vβ17" refers to a specific human β-chain variable region of three T cell receptors. Vβ17 has the following amino acid sequence: MSNQVLCCVVLC FLGANTVDGGITQSPKYLFRKEGQNVTLSCEQNLNH DAMYWYRQDPGQGLRLIYYSQIVNDFQKGD IAEGYSVSREKKESFPLTVTSAQKNPTAFYLCASS (SEQ ID No. 7).

"Vβ14" refers to a specific human β-chain variable regions of another TCR. Vβ14 has the following amino acid sequence: MGPQLLGYVVLCLLGAGPLEAQVTQNP RYLITVTGKKLTVTCSQNMNHEYMSWYRQDPGL GLRQIYYSMNVEVTDKGDVPEGYKVSRKEKRNFPLI LESPSPNQTSLYFCASS (SEQ ID No. 8).

"Vβ3" refers to a family of specific human β-chain variable region. Two members of the Vβ3 family have been identified as Vβ3.1 and Vβ3.2. Vβ3.1 has the following amino acid sequence: MGIRLLCRVAFCFIAVGLVDV KVTQSSEYLCKERFWKCDLWXCSMSHWNMDQYE USPFLFLELIYDAYSCKMKWKFSIPEGYSVSREKKE RFSLILESASTNQTSMYLCASS (SEQ ID No. 9). Vβ3.2 has the following amino acid sequence: MGIRLLCRVAFC FLAVGLVDVKVTQSSRYLVKRTGEKVFLECVDMDHE NMFWYQRQDPGLGLRLIYFSYDVKMKEKGD IPEGYSVSREKKERFSLILESASTNQTTSMYLCASS (SEQ ID NO:10).

The hypervariable or junctional regions are useful for the vaccines of the present invention. Hypervariable regions useful in the present invention include CDR1, CDR2, CDR3 and CDR4. The amino acid sequences of the CDR1, CDR2 and CDR4 hypervariable regions for Vβ3, Vβ14 and Vβ17 are shown in FIG. 1.

The CDR3, also known as the V(D)J region, is useful as a vaccine of the present invention since T cell immunity elicited by peptides corresponding to this region is expected to be highly specific for a particular antigen. Due to the recombination of the V, D and J region genes prior to maturation, the amino acid sequence across these regions is virtually unique to each T cell and its clones.

However, as a germ-line element, the CDR2 region is also useful in human diseases such as MS and in particular RA. In RA studies, the results indicate a limited number of Vβs among the activated T cells infiltrating the synovial target tissue with only a few incidences of sequence homology in the BVDJ region. Thus, peptides corresponding to the CDR2 region are viable alternatives for use as vaccines of the present invention. For example, the CDR2 region of Vβ3, DPGLGLRLIYFSYDVKMKEKG (SEQ ID No.72), of Vβ14, DPGLGLRQIYYSMNVEVTDKG (SEQ ID No.73), or of Vβ17, DPGQGLRLIYYSQIVNKFQKG (SEQ ID No.74), can be used.

Modifications in these sequences that do not affect the ability of the receptor or an immunogenic fragment thereof to act as an immunogen to stimulate the desired immune response are contemplated and are included in the definition of TCR fragment. The variable region can be joined with any D and J segment of the TCR. Further, immunogenically representative fragments of Vβ3, Vβ14 and Vβ17 are also included in the definition of "Vβ3," "Vβ14" and "Vβ17," respectively.

By "substantially pure," it is meant that the TCR is substantially free of other biochemical moieties with which it is normally associated in nature. Such substantially pure TCRs or fragments thereof, for instance, can be synthesized, produced recombinantly by means known to those skilled in the art. In addition, whole TCRs can be enzymatically treated to produce such fragments.

In another embodiment, vaccine peptides can correspond to the Vβ regions that contain sequences of high homology which are conserved among pathogenic TCRS. These regions of conserved homology include the conventional CDRs, such as CDR1 and CDR2, which are common to T cells bearing the same Vβ, and also the superantigen binding site, which can be common to pathogenic TCRs bearing different Vβs. The superantigen binding site is also known to be in or around the CDR4 hypervariable region.

The vaccines of the present invention comprise peptides of varying lengths corresponding to the TCR or immunogenic fragments thereof. The vaccine peptides can correspond to regions of the TCR which distinguish that TCR from other nonpathogenic TCRS. Such specific regions can, for example, be located within the various region(s) of the respective TCR polypeptide chains, for example, a short sequence spanning the V(D)J junction, thus restricting the immune response solely to those T cells bearing this single determinant.

The vaccines are administered to a host exhibiting or at risk of exhibiting an autoimmune response. Definite clinical diagnosis of a particular autoimmune disease warrants the administration of the relevant disease-specific TCR vaccines. Prophylactic applications are warranted in diseases where the autoimmune mechanisms precede the onset of overt clinical disease (for example, Type I Diabetes). Thus, individuals with familial history of disease and predicted to be at risk by reliable prognostic indicators could be treated prophylactically to interdict autoimmune mechanisms prior to their onset.

TCR peptides can be administered in many possible formulations, including pharmaceutically acceptable mediums. In the case of a short peptide, the peptide can be conjugated to a carrier, such as KLH, in order to increase its immunogenicity. The vaccine can include or be administered in conjunction with an adjuvant, of which several are known to those skilled in the art. After initial immunization with the vaccine, further boosters can be provided. The vaccines are administered by conventional methods, in dosages which are sufficient to elicit an immunological response. Such dosages can be easily determined by those skilled in the art.

Appropriate peptides to be used for immunization can be determined as follows. Disease-inducing T cell clones reactive with the target antigens are isolated from affected individuals. Such T cells are obtained preferably from the site of active autoaggressive activity such as a lesion in the case of pemphigus vulgaris, the central nervous system (CNS) in the case of multiple sclerosis or the synovial fluid or tissue in the case of rheumatoid arthritis. Alternatively, such T cells can be obtained from blood of affected individuals. The TCR genes from these autoaggressive T cells are then sequenced. Polypeptides corresponding to TCRs or portions thereof that are selectively represented among disease inducing T cells (relative to non-pathogenic T cells) can then be selected as vaccines and made and used as described above. An alternative method for isolating pathogenic T cells is provided by Albertini in PCT Publication No. WO88/10314, published on Dec. 29, 1988.

Alternatively, the vaccines can comprise anti-idiotypic antibodies which are internal images of the peptides described above. Methods of making, selecting and administering such anti-idiotype vaccines are well known in the art. See, for example, Eichmann, et al., *CRC Critical Reviews in Immunology* 7:193–227 (1987), which is incorporated herein by reference.

In a further aspect of the present invention, methods of preventing the proliferation of T cells associated with a T cell mediated pathology are also contemplated. Such methods include determining a T cell receptor binding partner according to the above methods and administering an effective amount of such binding partner in an appropriate form to prevent the proliferation of the T cells. The methods can be used, for example, to build a tolerance to self antigens as in the case of an autoimmune disease.

The present invention also relates to other methods of preventing or treating a T cell pathology by inhibiting the binding of a T cell receptor to its TCR binding partner in order to prevent the proliferation of T cells associated with the T cell pathology. Ligands that are reactive with the T cell receptor or its binding partner at binding sites that inhibit the T cell receptor attachment to the binding partner can be used. Such ligands can be, for example, antibodies having specificity for the T cell receptor or its binding partner.

The invention also provides a method of preventing or treating a T cell mediated pathology in an individual comprising cytotoxically or cytostatically treating a Vβ-containing T-cells, particularly Vβ3, Vβ14 and Vβ17, in the individual. The Vβ-containing T cells are treated with a cytotoxic or cytostatic agent that selectively binds to the Vβ region of a T cell receptor that mediates a pathology, such as RA or MS for example. The agent can be an antibody attached to a radioactive or chemotherapeutic moiety. Such attachment and effective agents are well known in the art. See, for example, Harlow, E. and Lane, *Antibodies. A Laboratory Manual*, Cold Spring Harbor Laboratory (1988), which is incorporated herein by reference.

Rheumatoid Arthritis

Rheumatoid arthritis (RA) is a T cell mediated autoimmune disease. The invention describes clonal infiltrates of activated Vβ3, Vβ14 and Vβ17 T cells in the synovium of rheumatoid arthritis patients. The presence of these T cells in the diseased tissue of most of patients examined, their clonality, and the cytotoxic activity of one such T cell for synovial adherent cells, demonstrate a central role for T cells bearing these Vβs in the pathogenesis of RA.

Activated T cell populations in the synovial tissue of RA patients have been examined by analyzing T cell receptor (TCR) mRNAs isolated from IL-2 receptor positive (IL-2R+) synovial T cells. As described in Example X(C), TCR mRNAs were amplified using a polymerase chain reaction (PCR) protocol designed to amplify human TCR β-chain genes containing virtually any desired Vβ gene element. In this analysis, clonal Vβ17 rearrangements were found to be enriched in the IL2-R+ population, indicating that Vβ17 T cells are likely involved in the pathogenesis of RA. A CD4+, Vβ17 bearing T cell clone has been isolated from one of the synovial tissue specimens and its in vitro cytotoxicity for synovial adherent cells supports the direct involvement of Vβ17 T cells in RA.

Additional studies were conducted to ensure that the prevalence of Vβ17 T cells in the initial studies did not result from an amplification bias for the Vβ consensus primer, and to examine the involvement of other TCR Vβ gene families in RA. As described in Example XI, RNAs from activated (IL2-R+) synovial T cells were analyzed by PCR-amplification with a panel of Vβ-specific PCR primers. In this analysis, Vβ17 transcripts were found in four of the five patients tested, confirming the association of Vβ17 with RA and validating the utility of the Vβ consensus primer. In addition, Vβ14 was found in four of the five RA patient samples and Vβ3 and Vβ9 were detectable in three of five patients.

The sequences of these various Vβ polypeptides were examined for homology to Vβ17. The results are in Table 1.

TABLE 1

Relative Homologies of TCR β Chain Polypeptides With Human Vβ17

| hVβ | 100% | (94aa) |
|---|---|---|
| mVβ6 | 69.1% | (94aa) |
| hVβ3 | 58.5% | (94aa) |
| hVβ12.1 | 53.2% | (94aa) |
| hVβ14 | 52.1% | (94aa) |
| mVβ7 | 51.7% | (89aa) |
| hVβ9 | 33.0% | (94aa) | hVβ = human Vβ
mVβ = mouse Vβ

As shown in Table 1, mouse Vβ6 is most closely homologous, followed by hVβ3, hVβ12.1, hVβ14, and mVβ7. Three of the human Vβs, Vβ3, Vβ14 and Vβ17, were detected in the synovium of RA patients. Vβ12.1 was negligible in the synovium despite considerable overall homology with Vβ17. In contrast, Vβ9 was found in three of five synovial samples, yet is only weakly homologous to Vβ17.

A surprising discovery is the greater homology found among all of the Vβs detected in the synovia of RA patients, except Vβ9, in a contiguous stretch of 15 amino acids located carboxy to the CDR2 region. The 15 amino acid sequences of these Vβs as well as other human and mouse Vβs are shown in Table 2. Within the β-chain, this region of conservation corresponds positionally to that previously shown to contain superantigen binding sites.

TABLE 2

Proposed Superantigen Binding Site in RA Associated Vβ Genes

| | | % H[1] | Seq. ID. No. |
|---|---|---|---|
| hVβ17 | EGYSVS<u>REKKE</u>SFPL | | 11 |
| hVBβ3 | EGYSVS<u>REKKE</u>RFSL | 86.7 | 12 |
| hVβ14 | EGYKVS<u>REKE</u>KRNFPL | 66.7 | 13 |
| hVβ12.1 | DGYSVSRSKTEDFLL | 66.7 | 14 |
| hVβ9 | NRFSPKSPDKAHLNL | <30 | 15 |
| mVβ6 | EGYDAS<u>REKKS</u>SFSL | 73.3 | 16 |
| mVβ7 | KGYRVSRRK<u>REH</u>FSL | 64.3 | 17 |
| mVβ8.2a | DGYKASRPSQENFSL | | 18 |
| mVβ8.2c | ..........KE... | | 19 |
| hVβ13.2 | DGYNVSRLKKQNFLLGLE | | 20 |

[1] % H = % homology compared with Vβ17

The exogenous superantigen, $SEC_2$, stimulates human Vβ13.2 T cells as a result of binding to a site on Vβ13.2 as described in Choi et al., *Nature* 346:471–473 (1990), which is incorporated herein by reference. The sequence of this binding site is shown in Table 2 as the last 11 amino acids for Vβ13.2.

A binding site for Mls-1a, an endogenous superantigen, has also been mapped to this region as described in Pullen et al., Cell 61:1365–1374 (1990), which is incorporated herein by reference. Identification of this region as the Mls binding site involved the study of V62 8.2a, the Vβ8.2 isoform common to laboratory mice, and Vβ8.2c, a β-chain found in wild mice. These β-chain polypeptides are distinguished functionally by their differential reactivities with Mls-1a and structurally by a difference of five amino acids. Of particular importance are the residues at position 70 and 71. The responder β-chain, Vβ8.2c, has lysine and glutamic acid, respectively, at these positions. Specific mutagenesis of the non-responder gene to encode a lysine-glutamic acid pair at positions 70 and 71 rendered that non-responder β-chain Ml-1a-reactive. This confirms the region as one of superantigen binding. Thus, both these exogenous and endogenous superantigens can bind in the vicinity of the 15 amino acid sequence homology identified in Table 2. In addition, the lysine-glutamic acid pair charge motif is implicated in Mls-1a reactivity. Involvement of this charge motif in Mls-1a reactivity is confirmed by its presence in mouse Vβ6 and Vβ7, two other Mls-1a reactive murine β-chains. The Vβ8.2c, Vβ6 and Vβ7 charge motif of a lysine or arginine followed by a glutamic acid residue is underlined in Table 2. Thus, the superantigen binding site for Mls-1a is characterized by this charge motif contained within the region of local homology.

The present invention is directed to the unexpected discovery that human Vβ3, Vβ14 and Vβ17 have a region that corresponds to the Mls-1a binding site. These three human Vβs display a significant degree of overall homology within the entire 94 amino acid sequence and of local homology within the 15 amino acid sequence with mVβ6 and mVβ7. Each of these Vβs possess a lysine or arginine/glutamic acid pair, which are underlined in Table 2 and represent what is meant by the term "charge motif." Vβ12.1, while displaying a high degree of overall and local homology with Vβ3, Vβ14 and Vβ17, lacks the charge motif, perhaps accounting for its presence in the synovium of only one of five RA patients. Vβ9 shows no overall or local homology to Vβs 3, 14 or 17 and lacks the charge motif.

The presence of Vβ3, Vβ14 and Vβ17-bearing T cells has been demonstrated among the activated synovial T cells in RA. These three β-chain polypeptides, in contrast to other known Vβs, possess overall and local sequence homology and an apparent superantigen binding charge motif. These results indicate that Vβ-specific T cell activation by superantigen plays a role in RA.

Vβ3, Vβ14 and Vβ17 are the only known human Vβ chains to possess this apparent superantigen binding site characterized by this local sequence homology and the identified charge motif. However, it is possible that other Vβs may become known that contain such binding sites. Thus, a substantially pure Vβ3, Vβ14 or Vβ17 sequence containing the charge motif can be used as an immunogen in the vaccines of the present invention. For example, the sequences or fragments thereof shown in Table 2 for Vβ3, Vβ14 and Vβ17 can be used. Vaccines containing any combination of these three Vβsequences, including all three sequences, can be used effectively to ameliorate T cell associated diseases.

In addition, other common V(D)J sequences of the β-chain observed in RA patients are listed in Table 3. The results taken from two different RA studies show sequence homologies in the βVDJs from four different clones, which indicates the usefulness of peptides corresponding to the CDR3 region as appropriate vaccine candidates.

TABLE 3

β-Chain VDJ Sequences Found in Common in RA Patients

| Patient | Vβ | VDJ Sequence | Jβ | Seq. ID No. |
|---|---|---|---|---|
| 1012 | Vβ14 | A S S L G G A V S - Y N | Jβ2.1 | 3 |
| 1013 | Vβ3 | A S S L G G E E T Q Y F | Jβ2.5 | 4 |
| C | Vβ3 | A S S L G G F E T Q Y F | Jβ2.5 | 5 |
| A | Vβ3 | A S S L G G T E A - F F | Jβ1.1 | 6 |

As noted, the invention provides the discovery that specific variable regions of the β-chains of three TCRS, designated Vβ3, Vβ14, and Vβ17, are closely associated with T cell mediated pathologies, especially rheumatoid arthritis in human subjects. This discovery allows for the detection, prevention and treatment of rheumatoid arthritis using the methodology set out in this invention. Similar therapeutic approaches set out above for EAE can be applied to rheumatoid arthritis by those skilled in the art.

Specifically, the invention provides a method of diagnosing or predicting susceptibility to T cell mediated pathologies in an individual comprising detecting T cells having the β-chain variable region from Vβ3, Vβ14 or Vβ17 in a sample from the individual, the presence of abnormal levels of such Vβ-containing T cells indicating the pathology or susceptibility to the pathology. The Vβ-containing T cells can be qualitatively or quantitatively compared to that of normal individuals. Such diagnosis can be performed, for example, by detecting a portion of the Vβs that does not occur on non-rheumatoid arthritis associated β-chain variable region T-cell receptors. The Vβs of the present invention can be detected, for example, by contacting the Vβs with a detectable ligand capable of specifically binding to the individual Vβs. Many such detectable ligands are known in the art, e.g. an enzyme linked antibody. Alternatively, nucleotide probes, complementary to the individual Vβ of interest, encoding nucleic acid sequences can be utilized to detect such Vβ-containing T cells, as taught, for instance, in Examples X and XI.

The invention also provides a method of preventing or treating a T cell mediated pathology comprising preventing the attachment of a Vβ3-, Vβ14- or Vβ17-containing T-cell receptor to its binding partner. In one embodiment, attachment is prevented by binding a ligand to Vβ3, Vβ14 or Vβ17. In an alternative embodiment, attachment is prevented by binding a ligand to the Vβ3, Vβ14 or Vβ17 binding partner. Attachment can be prevented by known methods, e.g. binding an antibody to the individual Vβs or to its binding partner in order to physically block attachment.

Multiple Sclerosis

T cells causative of multiple sclerosis (MS) have not previously been identified, though MBP-reactive T cells have been proposed to play a role due to the clinical and histologic similarities between MS and EAE. In rat and mouse models of EAE, MBP-reactive, encephalitogenic T cells show striking conservation of β-chain V(D)J amino acid sequence, despite known differences in MHC restriction and MBP-peptide antigen specificity. One embodiment of the invention is premised on the observation that a human myelin basic protein (MBP)-reactive T cell line, derived from an MS patient, has a TCR β-chain with a V(D)J amino acid sequence of Vβ4 homologous with that of β-chains from MBP-reactive T cells mediating pathogenesis in experimental allergic encephalomyelitis (EAE), an animal model of MS, as shown in Table 4. This finding demonstrates the involvement of MBP-reactive T cells in the pathogenesis of MS and demonstrates that TCR peptides similar to those described herein for the prevention of EAE can be appropriate in treating MS. As shown in Table 4, a VDJ sequence of Vβ12, CAIGSNTE (SEQ ID No. 2) and one of Vβ4, SGDQGGNE (SEQ ID No. 1), have been observed in MS patients.

TABLE 4

β-Chain VDJ Sequences in MS Patients Homologous to Rat VDJ Sequences

| Vβ | VDJ Sequence | SEQ ID Nos. |
|---|---|---|
| RAT Vβ8.2 | S S D S S N T E | 21 |
| RAT Vβ8.2 | S S D S G N T E | 22 |
| HUMAN Vβ4 | S G D Q G G N E | 1 |
| HUMAN Vβ12 | C A I G S N T E | 2 |

The activated cells of one MS patient from the CSF were analyzed and found to be predominantly Vβ14 and Vβ3. In both cases, there was a predominate clone of Vβ14 and a predominate clone of Vβ3. These findings indicate that the results from the RA studies relating to the same Vβs can be extended to other autoimmune pathologies, including MS.

In this regard, the invention is directed to the discovery that β-chain VDJ fragments homologous to VDJ sequences found in rodent EAE, such as SGDQGGNE (SEQ ID No.1) and CAIGSNTE (SEQ ID No. 2), are closely associated with multiple sclerosis in human subjects. This discovery allows for the detection, prevention and treatment of multiple sclerosis using the methodology set out in this invention. Similar therapeutic approaches set out herein for EAE can be applied to multiple sclerosis by those skilled in the art.

Specifically, the invention provides a method of diagnosing or predicting susceptibility to multiple sclerosis in an individual comprising detecting T cells having various Vβs, such as Vβ4 or Vβ12, and particularly having substantially the sequence SGDQGGNE (SEQ ID No.1) or CAIGSNTE (SEQ ID No.2), in a sample from the individual, the presence of the sequence indicating multiple sclerosis or susceptibility to multiple sclerosis. The sequences can be detected, for example, by contacting T cells or TCRs with a detectable ligand. Many such ligands are known in the art, for example, an enzyme linked or otherwise labeled antibody specific for the sequence. Alternatively, nucleotide probes complementary to the nucleic acid encoding the sequence can be utilized as taught, for instance, in Example IX.

The invention also provides a method of preventing or treating multiple sclerosis comprising preventing the attachment of a T-cell receptor containing various Vβs, including Vβ4, Vβ12 or fragments thereof, such as those having substantially the SGDQGGNE (SEQ ID No.1) or CAIGSNTE (SEQ ID No.2) sequence to its binding partner. In one embodiment, attachment is prevented by binding a ligand to the sequence. In an alternative embodiment, attachment is prevented by binding a ligand to the binding partner. Attachment can be prevented by known methods, such as binding an antibody to these Vβs, and in particular to the SGDQG-GNE (SEQ ID No.1) or CAIGSNTE (SEQ ID No.2) sequences, to physically block attachment.

The invention also provides a method of preventing or treating multiple sclerosis in an individual comprising cytotoxically or cytostatically treating T cells containing various Vβs, including Vβ4, Vβ12 and fragments thereof, particularly those having substantially the SGDQGGNE (SEQ ID No.1) or CAIGSNTE (SEQ ID No.2) sequence in the individual. In one embodiment, T-cells are treated with a cytotoxic or cytostatic agent which selectively binds to these Vβs or their immunogenic fragments. The agent can be, for example, an antibody attached to a radioactive or chemotherapeutic moiety.

T Cell Pathologies of Malignant Etiology

To illustrate the utility of TCR vaccination, autoimmune disease has been discussed. However, T cell lymphoma is another T cell pathology which would be amenable to this type of treatment. Application of this technology in the treatment of T lymphoma would be conducted in virtually identical fashion. In one respect, however, this technology is more readily applied to T cell proliferative disease since the isolation of the pathogenic T cells is more easily accomplished. Once the clones are isolated, the technology is applied in the manner described herein. Specifically, the TCR genes of the T lymphomas are sequenced, appropriate regions of those TCRs are identified and used as vaccines. The vaccines can comprise single or multiple peptides, and can be administered in pharmaceutically acceptable formulations, with or without adjuvants, by conventional means.

Gene Therapy

The present invention further relates to an alternative method of treating or preventing a T cell mediated pathology by gene therapy. In this method, a nucleic acid encoding for a TCR or an immunogenic fragment thereof is first inserted into an appropriate delivery system, for example a plasmid. The nucleic acid can be DNA or RNA encoding for TCRs, immunogenic fragments thereof or anti-idiotype antibodies that can be used as vaccines in the present invention. Such DNA or RNA can be isolated by standard methods known in the art. The isolated nucleic acid can then be inserted into a suitable vector by known methods. Such methods are described, for example, in Maniatis et al., *Molecular Cloning: A Laboratory Manual* (Cold Spring Harbor Laboratory 1982), which is incorporated herein by reference.

The vector is subsequently administered directly into a tissue of an individual. Preferably, the DNA or RNA-containing vector is injected into the skeletal muscle of the individual. For example, a 1.5 cm incision can be made to expose the quadricep muscles of the subject. A 0.1 ml solution containing from 10–100 μg of a DNA or RNA plasmid and 5–20% sucrose is injected over 1 minute into the exposed quadricep muscles about 0.2 cm deep. The skin is thereafter closed. The amount of DNA or RNA plasmid can range from 10 to 100 μl of hypotonic, isotonic or hypertonic sucrose solutions or sucrose solutions containing 2 mM CaCl$_3$. The plasmid containing solutions can also be administered over a longer period of time, for example, 20 minutes, by infusion. The in vivo expression of the desired gene can be tested by determining an increased production of the encoded polypeptide by the subject according to methods known in the art or as described, for example, in Wolff et al., *Science* 247:1465–1468 (1990).

It is believed that the treated cells will respond to the direct injection of DNA or RNA by expressing the encoded polypeptide for at least about 60 days. Thus, the desired TCR, immunogenic fragment or anti-idiotype antibody can be effectively expressed by the cells of the individual as an alternative to vaccinating with such polypeptides.

The present invention also relates to vectors useful in the gene therapy methods and can be prepared by methods known in the art. Compositions containing such vectors and a pharmaceutically acceptable medium are also provided. The pharmaceutically acceptable medium should not contain elements that would degrade the desired nucleic acids.

The following examples are intended to illustrate but not limit the invention.

EXAMPLE I

Rat Model of EAE

Female Lewis rats, (Charles River Laboratories, Raleigh-Durham, N.C.) were immunized in each hind foot pad with 50 μg of guinea pig myelin basic protein emulsified in complete Freund's adjuvant. The first signs of disease were typically observed 9–11 days post-immunization. Disease severity is scored on a three point scale as follows: 1=limp tail; 2=hind leg weakness; 3=hind leg paralysis. Following a disease course of approximately four to six days, most rats spontaneously recovered and were refractory to subsequent EAE induction.

EXAMPLE II

Selection and Preparation of Vaccines

Vaccinations were conducted with a T cell receptor peptide whose sequence was deduced from the DNA sequence of a T cell receptor beta gene predominating among EAE-inducing T cells of B10.PL mice. The DNA sequence was that reported by Urban, et al., supra, which is incorporated herein by reference. A nine amino acid peptide, having the sequence of the VDJ junction of the TCR beta chain of the mouse, was synthesized by methods known to those skilled in the art. The sequence of this peptide is: SGDAGGGYE (SEQ ID No.23). (Amino acids are represented by the conventional single letter codes.) The equivalent sequence in the rat has been reported to be: SSDSSNTE (SEQ ID No. 24) (Burns et al., J. Exp. Med. 169:27–39 (1989)). The peptide was desalted by Sephadex G-25 (Pharmacia Fine Chemicals, Piscataway, N.J.) column chromatography in 0.1 M acetic acid and the solvent was subsequently removed by two cycles of lyophilization. A portion of the peptide was conjugated to keyhole limpet hemocyanin (KLH) with glutaraldehyde at a ratio of 7.5 mgs of peptide per mg of KLH. The resulting conjugate was dialyzed against phosphate buffered saline (PBS).

EXAMPLE III

Vaccination Against EAE

Vaccines used in these studies consisted of free VDJ peptide and also of VW peptide conjugated to KLH. These were dissolved in PBS and were emulsified with equal volumes of either (1) incomplete Freund's adjuvant (IFA) or (2) complete Freund's adjuvant (CFA) made by suspending 10 mg/ml heat killed desiccated *Mycobacterium tuberculosis* H37ra (Difco Laboratories, Detroit, Mich.) in IFA. Emulsions were administered to 8–12 week old female Lewis rats in a final volume of 100 microliters per animal (50 μl in each of the hind footpads). 5 μg of unconjugated VDJ peptide were administered per rat. KLH-VDJ conjugate was administered at a dose equivalent to 10 μg of KLH per rat. Twenty-nine days later each rat was challenged with 50 μg of guinea pig myelin basic protein in complete Freund's adjuvant in the front footpads. Animals were monitored daily beginning at day 9 for clinical signs of EAE and were scored as described above. The results are presented in Table 5. As can be seen, not only was there a reduced incidence of the disease in the vaccinated individuals, but in those which did contract the disease, the severity of the disease was reduced and/or the onset was delayed. The extent of protection varied with the vaccine formulation, those including CFA as the adjuvant demonstrating the greatest degree of protection.

TABLE 5

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 1 | VDJ (IFA) | — | — | 2 | 3 | 3 | 3 | — | — | — |
| 2 | " | — | — | 1 | 3 | 3 | 3 | 2 | — | — |
| 3 | " | — | — | — | 3 | 3 | 3 | 2 | — | — |
| 4 | VDJ (CFA) | — | — | — | — | 1 | 1 | 1 | — | — |
| 5 | " | — | — | — | — | — | — | — | — | — |
| 6 | " | — | — | — | 1 | 3 | 3 | 3 | 2 | — |
| 7 | KLH-VDJ (CFA) | — | — | — | 1 | 3 | 2 | — | — | — |
| 8 | " | — | — | — | — | 1 | 1 | 1 | 1 | — |
| 9 | " | — | — | — | — | — | — | — | — | — |
| 10 | KLH-VDJ (IFA) | — | 1 | 3 | 3 | 2 | 2 | 1 | — | — |
| 11 | " | — | — | 3 | 3 | 3 | 3 | 3 | 2 | — |
| 12 | " | — | — | 1 | 3 | 3 | 3 | 3 | — | — |
| 13 | NONE | 1 | 3 | 3 | 3 | 3 | 1 | — | — | — |
| 14 | " | — | 1 | 3 | 3 | 3 | 1 | — | — | — |
| 15 | " | 1 | 3 | 3 | 3 | 1 | — | — | — | — |

Scoring: - no signs
1) limp tail
2) hind leg weakness
3) hind leg paralysis

EXAMPLE IV

Vaccination Against EAE With Lewis Rat VW Peptides

The VDJ peptide used in the previous examples was synthesized according to the sequence of TCR β chain molecules found on EAE-inducing T cells in BL0.PL mice. In addition, peptides were synthesized and tested which correspond to sequences found on encephalitogenic T cells in Lewis rats. These VDJ sequences are homologous with that of B10.PL mice, but not identical. The rat peptides were synthesized according to the DNA sequences reported by Burns, et al. and Chluba, et al., Eur. J. Immunol. 19:279–284 (1989). The sequences of these peptides designated IR1, 2, 3 and 9b are shown below, aligned with the B10.PL mouse sequence used in Examples I through III (VDJ):

| | | SEQ ID No. |
|---|---|---|
| VDJ | S G D A G G Y E | 23 |
| IR1 | C A S S D - S S N T E V F F G K | 25 |
| IR2 | C A S S D - S G N T E V F F G K | 26 |
| IR3 | C A S S D - S G N - V L Y F G E G S R | 27 |
| IR9b | A S S D - S S N T E | 28 |

The preparation, administration and evaluation of these vaccines were conducted as described in Examples I through III with the following exceptions: 50 μg of the individual VDJ peptides were incorporated into vaccine formulations containing CFA; neither vaccinations in IFA nor vaccinations with peptides conjugated to KLH were conducted. Control animals were untreated prior to MBP challenge as in Example III or were vaccinated with emulsions of PBS and CFA to assess the protective effect of adjuvant alone. The results are shown in Table 6 below.

TABLE 6

| Animal No. | Vaccination (Adjuvant) | Days After Challenge |    |    |    |    |    |    |    |    |
|------------|------------------------|----|----|----|----|----|----|----|----|----|
|            |                        | 10 | 11 | 12 | 13 | 14 | 15 | 16 | 17 | 18 |
| 1          | None                   | —  | 1  | 2  | 3  | 3  | 2  | —  | —  | —  |
| 2          | "                      | 1  | 3  | 3  | 3  | 2  | —  | —  | —  | —  |
| 3          | "                      | —  | 2  | 3  | 3  | 3  | 1  | —  | —  | —  |
| 4          | PBS-CFA                | 1  | 2  | 3  | 3  | 3  | —  | —  | —  | —  |
| 5          | "                      | 1  | 2  | 3  | 3  | 3  | —  | —  | —  | —  |
| 6          | "                      | —  | 2  | 3  | 3  | 3  | —  | —  | —  | —  |
| 7          | IR1 (50 μg)            | —  | —  | —  | 2  | 1  | —  | —  | —  | —  |
| 8          | "                      | —  | —  | —  | —  | 1  | 3  | —  | —  | —  |
| 9          | "                      | —  | —  | —  | 1  | 1  | 1  | 1  | —  | —  |
| 10         | IR2 (50 μg)            | —  | —  | 1  | 3  | 3  | 3  | —  | —  | —  |
| 11         | "                      | —  | —  | —  | —  | 2  | 2  | 3  | 3  | —  |
| 12         | "                      | —  | —  | —  | —  | 1  | —  | —  | —  | —  |
| 13         | IR3 (50 μg)            | 1  | 3  | 3  | 3  | 2  | —  | —  | —  | —  |
| 14         | "                      | —  | —  | 2  | 3  | 3  | —  | —  | —  | —  |
| 15         | "                      | —  | —  | —  | —  | —  | —  | —  | —  | —  |
| 16         | IR9b (50 μg)           | —  | —  | —  | —  | —  | —  | —  | —  | —  |
| 17         | "                      | —  | —  | —  | —  | —  | —  | —  | —  | —  |
| 18         | "                      | —  | —  | —  | —  | —  | —  | —  | —  | —  |
| 19         | "                      | —  | —  | —  | —  | —  | —  | —  | —  | —  |

Scoring: - no signs
1) limp tail
2) hind leg weakness
3) hind leg paralysis

As shown in Table 6, disease in unvaccinated control animals was observed as early as day 10. Disease was characterized by severe paralysis and wasting, persisted for 4 to 6 days and spontaneously remitted. PBS-CFA vaccinated rats displayed disease courses virtually indistinguishable from those of unvaccinated controls. In contrast, delays in onset were observed in some of the IR1, 2 or 3 vaccinated animals and others showed both delayed onset as well as decreased severity and/or duration of disease. Overall, however, vaccinations with the rat VDJ peptides (IR1-3) were slightly less effective than those with the mouse VDJ peptide (Example III). Vaccination with IR9b, however, afforded complete protection in all four animals in which it was tested. Importantly, no histologic lesions characteristic of disease were found in any of the four animals vaccinated with IR9b indicating that sub-clinical signs of disease were also abrogated.

EXAMPLE V

Vaccination With V Region Specific Peptides

A peptide specific for the Vβ8 gene family was tested as a vaccine against EAE. Vβ8 is the most common β chain gene family used by encephalitogenic T cells in both rats and mice. A peptide was synthesized based on a unique DNA sequence found in the Vβ8 gene, and which is not found among other rat Vβ genes whose sequences were reported by Morris, et al., Immunogenetics 27:174–179 (1988). The sequence of this Vβ8 peptide, designated IR7, is:

IR7 DMGHGLRLIHYSYDVNSTEK (SEQ ID No.29)

The efficacy of this Vβ8 peptide was tested in the Lewis rat model of EAE (Example I) as described in Examples II and III. 50 μg of peptide were tested in CFA. Vaccinations in IPA or with peptide-KLH conjugates were not conducted. The results of these studies are shown in Table 7.

TABLE 7

| Animal No. | Vaccination (Adjuvant) | Days After Challenge |    |    |    |    |    |    |    |    |
|------------|------------------------|----|----|----|----|----|----|----|----|----|
|            |                        | 10 | 11 | 12 | 13 | 14 | 15 | 16 | 17 | 18 |
| 1          | IR7 (50 μg)            | —  | —  | 1  | 2  | 3  | 3  | 3  | —  | —  |
| 2          | "                      | —  | —  | —  | —  | 1  | 1  | —  | —  | —  |
| 3          | "                      | —  | —  | —  | —  | —  | —  | —  | —  | —  |

Scoring: - no signs
1) limp tail
2) hind leg weakness
3) hind leg paralysis

EXAMPLE VI

Comparison of Vβ8.2 Peptide Lengths

The results of vaccinations conducted with the rat Vβ8 peptide are similar to those observed with the mouse and rat IR1, 2 and 3 peptides. Delayed onset as well as decreased severity and duration of disease was observed in one animal. One animal was completely protected.

It has been found that a corresponding 21 amino acid sequence of Vβ8.2 (residues 39–59) provided less protection than IR7 as shown in Table 8. The 21 amino acid sequence of Vβ8.2 is DMGHGLRLIHYSYDVNSTEKG (SEQ ID No.30).

TABLE 8

Comparison of Efficacy of Two β-Chain CDR2 Peptides in Protecting from EAE in the Lewis Rats (50)

| Vaccination | # With Disease # Tested | Mean Max Severity | Mean Onset | Mean Duration | # With Histology # Tested | Mean histology Score | Mean S.L. (14 days) |
|---|---|---|---|---|---|---|---|
| None | 10/10 | 2.8 | 10.5 | 8.4 | 10/10 | 3.7 | — |
| Control Peptide/ CFA | 9/10 | 2.8 | 11.5 | 8.1 | 9/9 | 2.6 | 1.0 |
| Vβ8.2$_{20}$ CFA | 6/16 | 1.3 | 11.2 | 3.8 | 8/10 | 1.0 | 16.4 |
| PBS/ CFA | 9/10 | 2.5 | 12.1 | 6.0 | 9/10 | 2.6 | — |
| Vβ8.2$_{21}$ CFA | 6/6 | 3.0 | 12.0 | 6.7 | 6/6 | 3.3 | 6.3 |

Each peptide was used at 100 μg doses and dissolved in saline prior to being emulsified in an equal volume of complete Freund's adjuvant (CFA). Animals were challenged after 42 days with 50 μg of guinea pig myelin basic protein in CFA. The CFA contained 10 mg/ml of mycobacteria tuberculosis. Injections and evaluation of clinical signs and histology were performed as previously described. Other animals (five per group) were immunized with peptides in the same way and their splenocytes were removed after 14 days to test for lymphocyte proliferation as described in Olee et al., J. Neuroimmunol. 21:235–240 (1989). The sequences of the 20 amino acid peptide and the 21 amino acid peptide are designated in Table 8 as Vβ8.2$_{20}$ and Vβ8.2$_{21}$ respectively.

EXAMPLE VII

Vaccination With J Region Peptides

A peptide was synthesized which corresponds to the J a gene segment, TA39, found among both rat and mouse encephalitogenic T cell receptors. The sequence of this peptide, designated IR5, is:

IR5 RFGAGTRLTVK (SEQ ID No.31)

The efficacy of the JαTA39 peptide was tested in the Lewis rat model of EAE (Example I) as described in Examples II and III. 50 µg of peptide were tested in CFA. Vaccinations in IFA or with peptide-KLH conjugates were not conducted. The results of these studies are shown in Table 9.

TABLE 9

| Animal No. | Vaccination (Adjuvant) | Days After Challenge | | | | | | | | | | |
|---|---|---|---|---|---|---|---|---|---|---|---|---|
| | | 10 | 11 | 12 | 13 | 14 | 15 | 16 | 17 | 18 | 19 | 20 |
| 1 | IR5 (50 µg) | — | — | — | — | — | — | 2 | 1 | 1 | 1 | 1 | — |
| 2 | " | — | — | — | — | — | — | — | — | — | — | — | — |
| 3 | " | — | — | — | — | — | — | — | — | — | — | — | — |

Scoring: - no signs
1) limp tail
2) hind leg weakness
3) hind leg paralysis

The results of vaccinations conducted with the rat J α TA39 peptide are more effective than those observed with the mouse VDJ peptide or the Vβ8 peptide. Two of three animals were totally protected and, in the third, disease onset was markedly delayed. Severity was also reduced in this animal though disease persisted for a normal course of 5 days. Importantly, the two animals which were completely protected showed no histologic evidence of T cell infiltration of the CNS. This result indicates that vaccinating with the J$_α$TA39 very efficiently induces a regulatory response directed at encephalitogenic T cells. Even sub-clinical signs of disease were abrogated.

EXAMPLE VIII

Vaccination With Mixtures of TCR Peptides

Vaccinations were conducted with a mixture of TCR peptides. This mixture contained 50 µg of each of the peptides IR1, 2, 3 and 5 (the three rat VDJ peptides and the rat JαTA39 peptide).

The efficacy of this peptide mixture was tested in the Lewis rat model (Example I) as described in Examples II and III. Peptides were tested in CFA. Vaccinations in IFA or with peptide-KLH conjugates were not conducted. The results of these studies are shown in Table 10.

TABLE 10

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 4 | IR1, 2, 3, 5 | — | — | — | — | — | — | — | — | — |
| 5 | (50 µg each) | — | — | — | — | — | — | — | — | — |
| 6 | " | — | — | — | — | — | — | — | — | — |

Scoring: - no signs
1) limp tail
2) hind leg weakness
3) hind leg paralysis

The results of vaccinations conducted with the rat JαTA39 and three VW peptides were as effective as those described for IR9b in Table 6. All three animals were totally protected. In addition to the absence of any clinical signs of EAE, two of these three animals were completely free of histological evidence of T cell infiltration into the CNS while the third showed only two small foci of lymphocytic infiltration at the base of the spinal cord.

EXAMPLE IX

Multiple Sclerosis Vaccine

A. Human MBP-Reactive T Cells

MBP-reactive T cell lines were established from peripheral blood mononuclear cells (PBMC) of nine chronic progressive MS patients and two healthy controls. Cells were maintained in culture by regular stimulation with purified human MBP and irradiated-autologous PBMC for three days followed by four days in IL-2 containing medium.

B. PCR Amplification of TCR β-Chain Genes From MBP-Reactive T Cell Lines

T cells were harvested from log phase cultures and RNA was prepared, amplified with the Vβ16mer primer and nested Cβ primers for 55 cycles as described in Example X.

C. TCR β-Chain Sequences of Human MBP-Reactive T Cells

Vβ16mer amplified TCR β-chain genes from human MBP-reactive T cell lines were sequenced using the Cβseq primer. Amplification products were gel purified, base denatured and sequenced from the Cβseq primer. Readable DNA sequence was obtained from 5 of these lines, indicating that predominant T cell clones had been selected by long term in vitro passage. One of these sequences, from the MS-Re cell line (Table 11), possessed a β-chain VDJ amino acid sequence that shared five of the first six and six of nine total residues with the β-chain VDJ amino acid sequence conserved among MBP reactive, encephalitogenic T cells in the B10.PL mouse model of EAE. This sequence was not present among the predominant TCR rearrangements found in the remaining four human MBP reactive T cell lines.

To determine if similar sequences were present in the β-chain repertoire of the MBP-reactive T cell lines from other MS patients, PCR amplification was conducted with a degenerate (n=1024) 21-nucleotide primer (VβRe) corresponding to seven amino acids of this sequence. RNAs were reversed transcribed and amplified in 20 cycle stage I reactions with the Vβ16mer and Cβext primers. One µl aliquots of these stage I reactions were reamplified for 35 cycles with the VβRe and Cβint primers. One µl aliquots of these reactions were analyzed by Southern blot hybridization with a $^{32}$P-labeled human Cβ probe. This analysis revealed the 300 bp amplified product in the Re cell line and in one of the other MS patient lines, but not in MBP-reactive T cells from control subjects or in non-MBP reactive human T cell lines and clones. The presence of this sequence in two of the nine MS patient lines tested is compelling. Since this sequence is known to be conserved among encephalitogenic T cells in EAE, its detection among MBP-reactive T cells from MS patients demonstrates a role for T cells bearing this determinant in the pathogenesis of MS.

Immunogenic peptides having the sequence SGDQGGNE (SEQ ID No.1) can be synthesized as shown in Example II and used to immunize human subjects by methods demonstrated in Example III. Such immunizations can result in an effective immune response.

TABLE 11

| Sample | Vβ | Dβ | Jβ | SEQ ID No. |
|---|---|---|---|---|
| A) | | | | |
| MS-Re | V84.2 | ctctgc agcggagaccagggcggc<br>S G D Q G G - | J52.1<br>aatgagcagttcttc<br>N E Q F F | 32<br>33 |
| B10.PL | | S G D A G G G Y E | | 23 |
| B) | | | | |
| | |       A           A   A<br>      C    A    C   C   C    A<br>5' GG GA CA GG GG AA GA 3'<br>      G   T    G   G   T    G<br>      T           T   T | | 34<br>35<br>36<br>37 |

EXAMPLE X

Detection of Clonal Infiltrates of Activated Vβ17 T Cells in the Synovium of Rheumatoid Arthritis Patients

A. T Cell Preparations From Synovial Tissue

Synovial tissue specimens were obtained from radiographically proven rheumatoid arthritis patients undergoing joint replacement therapy. Activated T cells were selected using magnetic beads and antibodies reactive with the human IL2-R (aIL2-R) as follows. Synovial tissue was digested for 4 hrs at 37° C. in RPMI+10% Fetal Bovine Serum (FBS) containing 4 mg/ml collagenase (Worthington Biochemical, Freehold, N.J.) and 0.15 mg/ml DNAse (Sigma, St. Louis, Mo.). Digests were passed through an 80-mesh screen and single cells were collected by Ficoll density gradient centrifugation. Cells at the interface were washed and were incubated at $10^6$/ml for 30 min at 0° C. with 5 μg/ml control mouse IgG (Coulter Immunology, Hialeah, Fla.) in PBS containing 2% FBS (PBS-FBS). Cells were washed three times and incubated for 30 min at 0° C. with magnetic beads conjugated to goat anti-mouse IgG (Advanced Magnetics, Cambridge, Mass.). Beads were magnetically separated and washed three times with PBS-FBS. This preselection with mouse IgG (mIgG) and magnetic beads was used to control for non-specific adsorption of T cells. The cells remaining in the initial suspension were further incubated 30 minutes at 0° C. with 5 μg/ml monoclonal mouse IgG reactive with the human T cell IL2-R (Coulter Immunology, Hialeah, Fla.). Cells were washed and selected with magnetic beads as above. Beads from the IgG preadsorption and the IL2-R antibody selection were immediately resuspended in acidified-guanidinium-phenol-chloroform and RNA prepared as described in Chonezynski and Sacchi, Anal. Biochem. 162:156 (1987), which is incorporated herein by reference. Since RNAS were prepared without in vitro culture of the cells and the accompanying bias that may be induced, they are expected to accurately reflect T cell distributions in synovial tissue at the time of surgical removal. Only half of the mIgG and αIL2-R beads from patient 1012 were immediately processed for RNA. The remainder were cultured for 5 days in RPMI 1640, 5% FBS, 20% HL-1 (Ventrex Laboratories Inc., Portland, Me.), 25 mM HEPES, glutamine, antibiotics and 20% LAK supernatant (Allegretta et al., Science, 247:718 (1990)), which is incorporated by reference herein, as a source of IL-2. RNA was extracted from cultures of the αIL2-R beads (1012IL2.d5), but not from the 1012mIgG sample as no viable cells were present at the end of the 5 day culture.

A T cell clone was derived from the Ficoll pellet of patient 1008. The cells in the pellet were cultured at $2 \times 10^6$/ml in media without IL-2 for two weeks. Non-adherent cells from this culture were cloned by limiting dilution onto autologous synovial cell monolayers. A CD4+ T cell clone 1008.8 was obtained and adapted to culture by regular stimulation with autologous synovial monolayers for 3 days in media without IL2 followed by a 4 day culture in medium with LAK supernatant.

B. Lysis of Synovial Adherent Cells By 1008.8

Lysis of synovial adherent cells by 1008.8 was demonstrated as follows. Synovial cell monolayers were labeled as described in Stedman and Campbell, J. Immunol. Meth. 119:291 (1989), which is incorporated herein by reference, with $^{35}S$ for use as targets in CTL assays. Cells were typsinized, washed and plated at 2000 cells per well of a 96-well round bottom microtiter plate. 1008.8 cells, cultured for 3 days prior to the assay with synovial adherent cells and medium containing LAK supernatant, were added to the targets at the indicated effector:target ratios. Cultures were incubated overnight at 37° C., centrifuged at 300×g for 2 minutes and radioactivity in 50 μl of the supernatant quantified. Per cent specific lysis was calculated relative to detergent-lysed targets by standard formulas. This clone is cytotoxic for synovial adherent cell targets in CTL assays (Table 12).

TABLE 12

| Effector:Target Ratio | % Specific Lysis |
|---|---|
| 5:1 | 7 |
| 10:1 | 16 |
| 25:1 | 32 |

C. PCR Amplification of TCR β-Chain Genes

TCR β-chain genes were amplified with several combinations of the primers shown in FIG. 2. The vβ16mer primer is a degenerate Vβ primer (n-256) which is predicted to bind 85% of human TCR β-chain genes at all 16 residues and 95% at 15 residues. This primer has been used to amplify TCR β-chains from more than 25 different human T cell clones, lines or primary tissue preparations. A spectrum of Vβ genes has been sequenced from these amplified DNAs, arguing against a significant bias of the primer for certain Vβ families. Thus, PCR amplification with the Vβ16mer primer facilitates analysis of T cell populations for which a Priori knowledge of Vβ gene usage is unavailable.

T cell receptor β-chain genes were amplified in two-stage amplification reactions with nested pairs of the primers shown in FIG. 2. The primer sequences used in the polymerase chain reactions are listed in Table 13.

TABLE 13

| | | | |
|---|---|---|---|
| VBcons | 5' | G AC    CAAA<br>T TC TGGTA    CA 3'<br>T TT    TCGT | (SEQ ID NO.47)<br>(SEQ ID NO.48) |
| Vβ17 | 5' | TCACAGATAGTAAATGACTTTCAG 3' | (SEQ ID NO.49) |
| Vβ8 | 5' | TCTCCACTCTGAAGATCC 3' | (SEQ ID NO.50) |
| Vβ12 | 5' | GATTTCCTCCTCACTCTG 3' | (SEQ ID NO.51) |
| 5'Cβ | 5' | CAAGCTGTTCCCACCCGA 3' | (SEQ ID NO.52) |
| Cβext | 5' | CCAGAAGGTGGCCGAGAC 3' | (SEQ ID NO.53) |
| Cβint | 5' | GCGGCTGCTCAGGCAGTA 3' | (SEQ ID NO.54) |
| Cβseq | 5' | CGACCTCGGGTGGGAACA 3' | (SEQ ID NO.55) |

RNAs were reverse transcribed for 1 hour at 42° C. with 40pmol of the Cβext primer in a 12 μl reaction using conditions described by Hart et al., The Lancet, p. 596 (1988), included by reference herein. Reactions were diluted with a master mix containing 40 pmols of the Vβ16mer primer, nucleotides and reaction buffer as above but without $MgCl_2$ to give a final $Mg^{+2}$ concentration of 3.6 mM. Samples were denatured for 15 minutes at 95° C., 1 unit of heat stable recombinant DNA polymerase (Cetus Corporation, Emeryville, Calif., Ampli-taq™) was added and 20 cycles of PCR conducted. Each cycle consisted of a 1 min denaturation at 95° C., a two minute annealing step and a two minute extension at 72° C. The first two cycles were annealed at 37° C. and 45° C., respectively, and the remainder at 50° C. One microliter aliquots of these stage I reactions were added to 100 μl stage II amplification reactions (Cetus, Gene-Amp Kit™) containing 100 pmols of the Cβint primer and 100 pmols of the Vβ8, Vβ17 or 5'Cβ primers or 700 pmols of the Vβ16mer primer. Stage II amplifications were conducted as above with a 50° C. annealing temperature and without the 37° C. and 45° C. ramping.

cycle stage II reactions. Reaction products, purified from low melting agarose gel slices with Gene Clean glass beads (Bio 1D1, San Diego, Calif.), were base denatured and sequenced from the Cβseq primer with T7 polymerase (Sequenase, United States Biochem, Cleveland, Ohio). A predominate Vβsequence, corresponding to a single Vβ17 rearrangement (Table 14), was clearly readable in the 1012IL2.d5 sample. Other, less frequent rearrangements were detected as faint, uninterpretable background bands in the sequencing gels. Culture of these 1012.IL2 cells in IL2-containing medium without added accessory cells or antigen is not expected to induce de novo activation of these T cells. Thus, the predominance of a single Vβ17 rearrangement in this sample reflects in vivo clonal expansion of Vβ17+ T cells in this patient. DNA sequence determination of TCR β-chain DNA amplified from the cytotoxic T cell clone, 1008.8, also revealed a Vβ17 rearrangement (Table 14). The presence of Vβ17 rearrangements in these two different types of synovial T cell samples, derived from two separate RA patients, implicates Vβ17 bearing T cells in the pathogenesis of RA.

TABLE 14

| Sample | Vβ | Dβ | Jβ | SEQ ID NO. |
|---|---|---|---|---|
| 1012<br>day 5 | Y L C A S<br>tatctctgtgccagt<br>Vβ17 | K N P T V S<br>aaaaatcccacggtctcc | Y G Y T F<br>tatggctacaccttc<br>Jβ1.2 | 38<br>39 |
| 1008.8 | Y L C A S<br>tatctctgtgccagt<br>Vβ17 | D N E S<br>gacaacgagagt | F F G Q G<br>ttctttggacaaggc<br>Jβ1.1 | 40<br>41 |
| 1014<br>IL-2 | Y L C A S<br>tatctctgtgccagt<br>Vβ17 | V R D R R<br>gtgagggacaggaga | N Y G Y T<br>aactatggctacacc<br>Jβ1.2 | 42<br>43 |
| 1015<br>IL-2 | Y L C A S<br>tatctctgtgccagtagt<br>Vβ17 | S S I D S S<br>agtatagactcc | Y E Q Y<br>tcctacgagcagtac<br>Jβ2.7 | 44<br>45 |

RNA samples from 1012IL2.d5 and 1008.8 cultures were amplified with the Vβ16mer and Cβext primers in stage I reactions and with the Vβ16mer and the Cβint primer in 35

To determine whether or not Vβ17 rearrangements were present in the other magnetic bead RNA preparations, TCR β-chain genes were amplified with a Vβ17-specific primer in the second stage amplification after an initial amplification with the Vβ16mer. Vβ17 TCR DNA could be amplified from magnetic bead samples derived from the 4 patients examined. Ethidium bromide staining of electrophoresed reaction products revealed greater Vβ17 amplification in some of the IL-2R+ samples than in the corresponding controls. Accordingly, the relative amounts of Vβ17 TCRs in each control and IL-2R+ sample were quantified by slot blot hybridization analysis as follows.

RNAs from magnetic bead preps were amplified in the first stage with the Vβ16mer and Cβext primers and then reamplified for twenty cycles with the Cβint primer and each of the Vβ17, Bβ8 and 5'Cβ primers. Amplification reactions were serially diluted in 20×SSC, denatured by boiling and chilled in an ice slurry. Samples were loaded onto nitrocellulose membranes, hybridized to a human TCR β-chain constant region probe and washed with 0.1×SSC, 0.1% SDS at 56° C. Bound radioactivity was quantified by liquid scintillation spectroscopy and endpoint dilutions were those samples with fewer than 200 cpm bound. The amounts of product produced by forty total cycles with each of the respective primer combinations falls in the linear portion of a product versus cycle number quantification curve.

Amplifications with the 5'Cβ and Cβint primer pair were used to estimate the total β-chain amplified from each sample, providing benchmarks for normalizing the results of Vβ17 and Vβ8 quantification in the respective IL-2R+ and control sample pairs (Table 15). The quantity of Vβ17 DNA amplified was increased in the IL-2R+ samples, relative to the control samples, in 3 of the 4 patients. The magnitude of the increase ranged from 5-fold in patient 1015 to 40-fold in patient 1014 (Table 15). This enrichment was not a product of the isolation procedure, since the quantity of Vβ8 DNA amplified was increased in the IL-2R+ fraction only in patient 1015.

Vβ17 rearrangements from the IL-2R+ RNAs of the three patients showing enrichment were amplified with the Vβ17 and Cβint primer pair and the reaction products sequenced with the Cβseq primer. As was shown for sample 1012 IL-2.d5, 1014 and 1015 contained single sequences (Table 14), indicative of clonal expansion of Vβ17 T cells in vivo. In contrast, direct sequencing of the rearrangements amplified with the Vβ8 specific primer was not possible due to significant heterogeneity in the β-chain product.

D. HLA-DR Analysis in Rheumatoid Arthritis Patients

HLA-DR analysis in rheumatoid arthritis patients was performed as follows. DNA from each patient was prepared by boiling $10^5$ synovial cells in 200 μl dH$_2$O. Ten μl were amplified for 35 cycles in a 100 μl reaction (Cetus, GENE AMP KIT™) containing 100 pmols of each of the DRβ PCR primers shown in Table 16 as DRβ1 (SEQ ID NO:56) and (SEQ ID NO:57) and DRβ3 (SEQ ID NO:69), (SEQ ID NO:70) and (SEQ ID NO:71). One-tenth μl of this reaction was reamplified in 10 μls containing only the DRβ2 primer (SEQ ID NO:58) and (SEQ ID NO:59) and 17 pmol of α32P-dCTP as the sole source of dCTP for 10 cycles. Reactions were spiked with 200 μM dCTP and chased for 2 cycles. The resulting negative strand probes were hybridized to slot blots containing 10 pmol of the HLA-DR allele specific oligos (positive strands) using conditions previously described by Amar et al., J. Immunol. 138:1947 (1987), which is incorporated herein by reference. The slots were washed twice for 20 minutes with tetramethylammonium-chloride (Wood et al., Proc. Natl. Acad. Sci. U.S.A. 82:1585 (1985)) which is incorporated herein by reference) at 65–68° C. and exposed to X-ray film.

Each of the patients in this study possessed at least one allele of the HLA-DR genes, DR4w4, DR1, DR4w14 or DR4w15, that are known to predispose for RA (Table 16). Also shown in Table 16 are HLA-DR allele specific oligonucleotides.

TABLE 15

| Sample | Endpoint Dilution | | | | Vβ17IL-2R | | Vβ8IL-2 |
| | Cβ | Vβ17 | Vβ8 | Vβ17/Cβ | mIgG | Vβ8/Cβ | mIgG |
| --- | --- | --- | --- | --- | --- | --- | --- |
| 1 | 3,125 | 3,125 | 625 | 1 | 25 | 0.2 | 1 |
| 2 | 3,125 | 125 | 625 | 0.04 | | 0.2 | |
| 3 | 15,625 | 25 | 625 | 0.001 | 0.12 | 0.04 | 0.04 |
| 4 | 3,125 | 25 | 3,125 | 0.008 | | 1 | |
| 5 | 15,625 | 625 | 125 | 0.04 | 40 | 0.008 | 0.04 |
| 6 | 3,125 | 5 | 625 | 0.001 | | 0.2 | |
| 7 | 15,625 | 625 | 15,625 | 0.04 | 5 | 1 | 25* |
| 8 | 78,125 | 625 | 3,125 | 0.008 | | 0.04 | |

Sample 1 = 1012 IL-2R+, Sample 2 = 1012 mIgG,
Sample 3 = 1013 IL-2R+, Sample 4 = 1013 mIgG,
Sample 5 = 1014 IL-2R+, Sample 6 = 1014 mIgG,
Sample 7 = 1015 IL-2R+, Sample 8 = 1015 mIgG.
*In a follow-up study in which Vβ8 was sequenced, it was found that the enrichment of this Vβ was an artifact and that the value is ≦ 1.

TABLE 16

|   |   | SEQ ID NO. |
|---|---|---|
| DRβ1 | 5' G A G T C T G G A A C A G C 3'<br>      A<br>      C | 56<br>57 |
| DRβ2 | 5' G T A G T T G T T C T G C A 3'<br>      A<br>      G | 58<br>59 |

HLA-DR ALLELE-SPECIFIC OLIGONUCLEOTIDES

DRβ1 Genes

| | | |
|---|---|---|
| DR1,DR4w14,DR4w15 | 5' CTC CTC GAG CAG AGG CGG GCC GCG 3' | 60 |
| DR2* | 5' T-- --- --- G-C --- --C --- --- 3' | 61 |
| DR3 | 5' --- --- --- --- -A- --- -G- CG- 3' | 62 |
| DR4w4 | 5' --- --- --- --- -A- --- --- --- 3' | 63 |
| DR4w13 | 5' --- --- --- --- --- --- --- -A- 3' | 64 |
| DR5, DR6, DR4w10 | 5' A-- --- --A G-C GA- --- --- --- 3' | 65 |
| DR7 | 5' A-- --- --- G-C --- --- -G- CA- 3' | 66 |
| DR8 | 5' T-- --- --A G-C --- --- --- CT- 3' | 67 |
| DR9 | 5' T-- --- --- -G- --- --- --- -A- 3' | 68 |

DRβ3 Genes

| | | |
|---|---|---|
| DR2 | 5' A-- --- --- --- GC- --- --- --- 3' | 69 |
| DR3 | 5' --- --- --- --- -A- --- -G- CAG 3' | 70 |
| DR7, DR9 | 5' --- --- --- -G- --- --- --- -A- 3' | 71 |

| Patient | HLA-DR |
|---|---|
| 1008 | 1,4w4 |
| 1012 | 1,3 |
| 1013 | 1,7 |
| 1014 | 1,4w4 |
| 1015 | 4w4,4w4 |

*The dashes refer to amino acids in common with DR1, DR4w14, DR4w15 T cell receptors containing Vβ17 or fragments T cell receptors containing Vβ17 or fragments thereof which are immunogenic or can be made immunogenic can be used to immunize human subjects by methods demonstrated by Example VIII. Such immunizations can result in an effective immune response.

EXAMPLE XI

Figure 3:
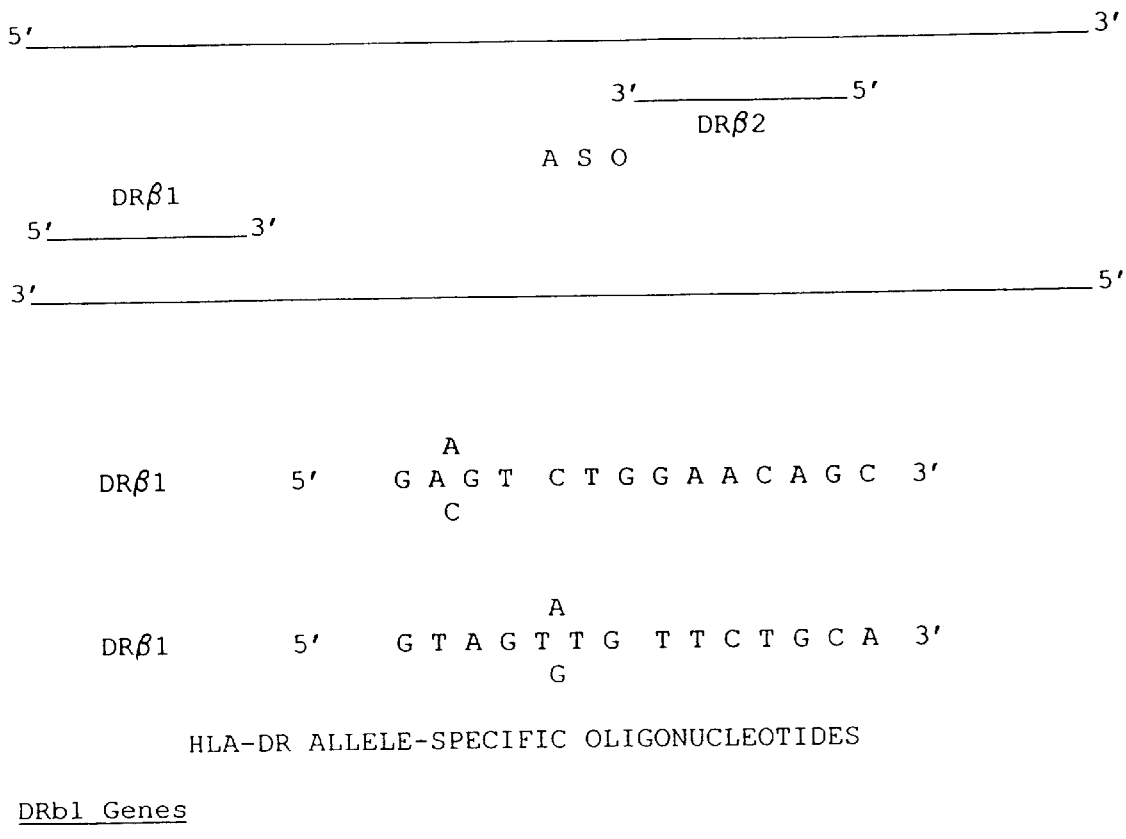
FIG. 3 shows the location and sequence of primers used in polymerase chain reaction amplification of HLA-DR $B_1$ genes (SEQ ID NOS:56 through 59, respectively). Also shown are HLA-DR allele specific oligonucleotides (SEQ ID NOS:60 through 71, respectively).

Synovial tissue specimens were obtained from proven RA patients undergoing joint replacement surgery. HLA-DR analysis was conducted as described in Example IX(D).
A. Polymerase Chain Reaction (PCR) Amplification of T Cell Receptor β-Chain Genes T cell receptor β-chain genes were amplified in two-stage amplification reactions with nested pairs of HPLC-purified oligonucleotide primers (Midland Certified Reagents, Midland, Tex.) shown in FIG. 3. RNAs were reverse transcribed (1 hour, 42° C.) with the Cβext primer (40 pmol) in 12 μl of reaction buffer (Hart et al., Lancet ii:596–599 (1988)). Reactions were diluted with a master mix (8 μl) containing the Vβcons primer (40 pmol), nucleotides and reaction buffer minus MgCl$_2$ (final Mg$^{+2}$ concentration=3.6 mM). Samples were denatured (15 minutes, 9° C.) and 20 cycles of PCR were conducted using Taq polymerase (1 unit, Cetus AMPLI-TAQ™). Each cycle consisted of a 1 minute denaturation at 95° C., a two minute annealing step and a two minute extension at 72° C. The first two cycles were annealed at 37° C. and 45° C. and the remainder at 50° C. One microliter aliquots of these Stage I reactions were added to 100 μl Stage II amplification reactions (Cetus Gene-Amp Kit) containing the Cβint primer (100 pmol) and either the Vβ8, Vβ12, Vβ17, or 5'Cβ primers (100 pmol) or the Vβcons primer (100–700 pmol). Stage II amplifications were conducted for the indicated number of cycles with a 50° C. annealing temperature and without the 37° C. and 45° C. ramping.

B. Vβ17 T Cells Are Cytotoxic For Synovial Adherent Cells

Two parallel cultures were established from single cell suspensions, derived by enzymatic digestion as described below from the synovial tissue of patient 1008. The first, a bulk culture of total synovial tissue cells, was plated at $2\times10^6$/ml in RPMI 1640, 5% FBS, 20% HL-1 (Ventrex Laboratories, Portland, Me.), 25 mM HEPES, glutamine and antibiotics. The culture was grown undisturbed for two weeks in the absence of exogenous antigen or growth factors. The second, a synovial cell monolayer culture, was initiated as above and regularly trypsinized and passaged during this two-week period. Monolayer cells were plated at $5\times10^4$ cells/well in flat-bottomed, 96-well microtiter plates and cultured overnight. Non-adherent cells from the total synovial cell culture were then plated at 10 cells/well onto the monolayers. Wells positive for T cell growth were expanded and adapted to culture by regular stimulation with autologous synovial monolayers for 3 days in media without IL-2 followed by a 4 day culture in medium containing 20% supernatant from lymphokine activated killer (LAK) cells, a source of IL-2 (Allegretta et al., *Science* 247:718–721 (1990)). Later passages were adapted to weekly stimulation with allogeneic PBLS and anti-CD3 antibody (Coulter Immunology, Hialeah, Fla.) in place of synovial cell monolayers.

Cytotoxicity assays were conducted as described Stedman et al., *Immunol. Meth.* 119:291–294 (1989), incorporated herein by reference, using $^{35}$S-labeled synovial monolayer cells or EBV-transformed B cells as targets. Target cells were labeled overnight, trypsinized (adherent cells only), washed and plated at 2000 cells per well in 96-well round bottom microtiter plates. T cells were activated with allogenic PBLs and anti-CD3 antibody in medium containing LAK supernatant for 7 days prior to the assay and added to the targets at the indicated effector:target ratios. Cultures were incubated overnight at 37° C., centrifuged at 300×g for 2 minutes and radioactivity in 50 $\mu$l of the supernatant quantified.

The per cent specific lysis was calculated relative to detergent-lysed targets as described in Townsend et al., *Cell* 44:959–968 (1986), incorporated herein by reference. At effector:target ratios of 1.0, 2.5 and 5.0, the percent lysis of synovial adherent cells by 1008.8 T cells was approximately 4%, 14% and 33%, respectively. By comparison, at the same effector:target ratios, 1008.8 T cells had no demonstrated effect on EBV-transformed B cell targets. Similarly, at the same effector:target ratios, the percent lysis of synovial adherent cells by MS3 cells was approximately 0%, 0% and 3%, respectively.

T cells were isolated from the synovial tissue of patient 1008 by co-cultivation with synovial cell monolayers. Since the antigens recognized by pathogenic T cells in RA are unknown, synovial cell monolayers were used as stimulators of in vitro synovial T cell growth. The relevant target cells were assumed to be present in a bulk adherent cell culture from diseased synovium. Of 192 microwell co-cultures plated, 7 were positive for T cell growth within 10–14 days. T cells were expanded and maintained in vitro by alternately stimulating with synovial cell monolayers and medium containing LAK supernatant. Flow cytometry revealed that each of these seven cultures was 100% CD4+. One culture designated 1008.8, grew especially vigorously and, as assessed microscopically promoted the destruction of the monolayer cells. CTL assays confirmed the cytotoxicity of 1008.8 for these monolayer targets as discussed above. Cytolysis was specific for synovial cell targets, as no lysis of autologous Epstein-Barr virus-transformed B cells was demonstrable. Neither of the targets was lysed by a CD4+, myelin basic protein-reactive human CTL clone, MS3, excluding the possibility that the monolayer cells were susceptible to lysis by any activated T cell. In repeated assays with 1008.8, specific lysis never exceeded 30–35%, suggesting that the relevant synovial target cell comprises approximately that proportion of the total monolayer culture, which based on morphology is a mixture of multiple cell types.

The T cell receptor (TCR) β-chain gene of 1008.8 was amplified by the polymerase chain reaction (PCR) as described in Mullis et al., *Meth. Enzvm.* 155:335–350 (1987), incorporated herein by reference, and its DNA sequence was determined. Amplification was accomplished using a consensus Vβ primer (Vβcons), a degenerate 16 nucleotide primer (n=256) which is homologous at all 16 residues with 78%, and at 15 of 16 residues with 98%, of known human TCR Vβ genes, which have been compiled by Kimura et al., *J. Immol.* 17:375–383 (1987). This primer was designed to amplify β-chain rearrangements containing any of the known Vβ genes, thus allowing analysis of T cell clones for which a priori knowledge of Vβ gene usage is unavailable. Sequencing of the Vβcons-amplified β-chain gene of 1008.8 revealed a single Vβ17-Jβ1.1 rearrangement as shown in Table 16. Subsequently, the remaining six cultures derived from patient 1008 were analyzed by PCR amplification using a Vβ17-specific primer shown in Table 13. TCR genes from three of those six were amplifiable, indicating that, of the 7 T cell cultures obtained from the synovium of this patient, 4 had rearranged and expressed the Vβ17 gene.

C. Vβ17 T Cells are Enriched Among Activated T Cells in RA Synovium

Synovial tissue was digested with agitation for 4 hrs at 37° C. in RPMI-1640 and 10% fetal bovine serum (FBS) containing 4 mg/ml collagenase (Worthington Biochemicals, Freehold, N.J.) and 0.15 mg/ml DNAse (Sigma Chemical, St. Louis, Mo.). Digests were passed through an 80-mesh screen and single cells were collected from the interface of Ficoll density gradients, washed and incubated at $10^6$/ml for 30 min at 0° C. with 5 $\mu$g/ml control mouse IgG (Coulter) in PBS containing 2% BSA. Cells were washed 3× and incubated for 30 min at 0° C. with magnetic beads conjugated to goat anti-mouse IgG (Advanced Magnetics, Cambridge, Mass.). After magnetic removal of the beads, the remaining cells were incubated 30 minutes at 0° C. with 5 $\mu$g/ml mouse anti-human IL-2R (Coulter), washed and selected with magnetic beads as above. Cell-coated beads from the mIgG preadsorption and the IL-2R antibody selection were washed 3×, immediately resuspended in acidified-guanidinium-phenol-chloroform and RNA was prepared as described in Chomczynski et al., *Anal. Biochem.* 162:156–159 (1987).

RNAs from magnetic bead preparations were reverse transcribed and amplified for 20 cycles in stage I reactions with the Vβcons and Cβext primers. One $\mu$l of each reaction was reamplified for 20 cycles in individual stage II reactions containing the Cβint primer in conjunction with the Vβ17, Vβ8, Vβ12 and 5'Cβ primers. Aliquots of each reaction were diluted in 20×SSC, denatured by boiling and chilled in an ice slurry. Samples were loaded onto nitrocellulose membranes, hybridized to a human TCR β-chain constant region probe and washed with 0.1×SSC, 0.1% SDS at 56° C. Bound radioactivity was quantified by liquid scintillation spectroscopy. The amounts of product produced by 40 total cycles with each of the respective primer combinations falls in the linear portion of a product versus cycle number quantification curve. Values shown in Table 17 below reflect the relative increase or decrease for the specific Vβs in the IL2-R+ versus mIgG controls calculated according to the formula:

$$\frac{\text{specific } V\beta \text{ cpms}(IL2-R+)/C\beta \text{ cpms}(IL2-R+)}{\text{specific } V\beta \text{ cpms }(mIgG)/C\beta \text{ cpms}(mIgG).}$$

TABLE 17

| Sample | Ratio IL-2R+ mIgG | | |
|---|---|---|---|
| Experiment # | Vβ17 | Vβ8 | Vβ12 |
| 1012 | | | |
| 1 | 1.88 | 0.42 | 1.35 |
| 2 | 1.60 | 0.39 | 0.72 |
| 3 | 2.11 | 0.48 | 0.64 |
| X⁻ ± S.D. | 1.86 ± 0.25 | 0.43 ± 0.04 | 0.900 ± 0.38 |
| 1013 | | | |
| 1 | 2.54 | 0.49 | N.D. |
| 2 | 3.65 | 0.87 | 0.87 |
| 3 | 4.29 | 2.07 | 0.96 |
| X⁻ ± S.D. | 3.49 ± 0.88 | 1.14 ± 0.82 | 0.91 ± 0.06 |
| 1014 | | | |
| 1 | 4.70 | 0.17 | N.D. |
| 2 | 1.68 | 0.10 | 1.50 |
| 3 | 1.92 | 0.09 | 0.44 |
| 4 | 2.34 | 0.07 | 0.55 |
| X⁻ ± S.D. | 2.66 ± 1.38 | 0.10 ± 0.04 | 0.83 ± 0.58 |
| 1015 | | | |
| 1 | 3.40 | 0.20 | 0.85 |
| 2 | 2.85 | 0.47 | 1.82 |
| X⁻ ± S.D. | 3.12 ± 0.50 | 0.38 ± 0.15 | 1.33 ± 0.68 |

Next, the presence of Vβ17 T cells in the synovial tissue of other RA patients was determined. Since the rheumatoid synovium contains a mixture of activated and non-activated T cells, the activated T cells were identified as the most relevant for the initiation and perpetuation of the disease pathogenesis. Thus, activated T cells from single-cell suspensions of synovial tissue were selected using magnetic beads and antibodies reactive with the human interleukin-2 receptor (IL-2R). Cell suspensions from each patient were pretreated with an isotype-matched mouse IgG (mIgG) and magnetic beads to control for non-specific adsorption. RNAs were directly extracted from cells in the IL-2R+ and control samples without in vitro culture and, therefore, are expected to accurately reflect T cell distributions in synovial tissue at the time of surgical removal.

The initial PCR amplifications of these magnetic bead RNA preparations revealed greater amounts of Vβ17 PCR product in the IL2-R+ samples than in the corresponding mIgG controls. The presence of TCR mRNA in the mIgG samples indicates that T cells non-specifically adhered to the magnetic beads. The apparent increase in Vβ17 PCR product in the IL2-R+ sample suggests that the activated T cell compartment contained more Vβ17 T cells than the unselected synovial T cell compartment. Thus, a quantitative PCR analysis was used to formally examine the relative proportions of Vβ17 T cells in the IL-2R+ and mIgG control samples (Table 17). Magnetic bead RNAs were reverse transcribed, preamplified with Vβcon and Cβext and reamplified in separate reactions with a constant region primer (Cβint) and each of the Vβ-specific primers, Vβ17, Vβ8 and Vβ12. The second stage amplification was also performed with two Cβ primers (5'Cβ and Cβint) in order to estimate the total β-chain present in each sample and to provide benchmarks for normalizing the results of specific Vβ quantification in the respective IL-2R+ and control sample pairs. The proportion of Vβ17 DNA, relative to total Cβ, was increased in the IL-2R+ samples over that found in the mIgG control samples for each of the 5 patients examined. This increase was observed in multiple analyses and the means are shown in Table 17. Enrichment was not a product of the isolation procedure, since the quantity of Vβ8 or Vβ12 DNA amplified was not significantly increased in the IL-2R+ fraction of any of the patients. Thus, activated T cells in the rheumatoid synovium do not represent a cross section of all possible Vβ families, but preferentially contain Vβ17 T cells, and possibly other Vβ families which were not quantified in this analysis.

D. Synovial Vβ17 T Cells Display Limited Heterogeneity

RNAs were reverse transcribed and amplified with the Vβcons and Cβext primers in 20 cycle stage I reactions and with the Cβint and Vβcons (1008.8) or Vβ8, Vβ12, and Vβ17 primers (magnetic bead RNA preparations) in 35 cycle stage II reactions. Double stranded reaction products were electrophoresed in 2% Nu-Sieve agarose gels. After purification from gel slices with Gene Clean (Bio 101, San Diego, Calif.), samples were base denatured and either directly sequenced or cloned into plasmid for sequencing of multiple independent rearrangements. In all cases, samples were sequenced from the Cβseq primer (FIG. 2) with T7 polymerase (Sequenase, United States Biochemicals, Cleveland, Ohio).

Vβ17 rearrangements present in the IL-2R+ RNAs were amplified from the Vβcons and Cβext preamplification with the Vβ17 and Cβint primer pair and the reaction products sequenced. PCR products from patients 1014 and 1015 were directly sequenced and the results obtained were consistent with the presence of a single Vβ17 rearrangement in each of these amplified samples (Table 17). The PCR product of patient 1013 was cloned into plasmid and the thirteen isolates that were sequenced contained identical Vβ17 rearrangements. Sequencing of plasmid clones from patient 1012 revealed the presence of two dominant rearrangements (5 isolates of each) and a single isolate of another. Thus, the Vβ17 repertoire in the RA synovium is of limited heterogeneity, indicative of clonal or oligoclonal expansion of Vβ17 T cells in vivo. This is in contrast to the Vβ8 and Vβ12 repertoires, from these same synovial preparations, which showed significant heterogeneity. None of the PCR-amplified Vβ8 and Vβ12 samples analyzed were directly sequenceable and plasmid cloning of Vβ8 rearrangements from patient 1012 revealed 4 different sequences in 5 clones analyzed.

Vβ17 rearrangements in PBLs from patient 1012 also revealed greater diversity than that seen in the synovial IL-2R+ sample. RNA from a 3 day culture of PHA/PMA stimulated 1012 PBLs was amplified with the Vβ17 primer, as for the synovial sample, and the products cloned into plasmid. Nine different rearrangements, none of which corresponded to those present in the 1012 synovium, were found in the 10 clones that were sequenced. Thus, the restricted heterogeneity of Vβ17 rearrangements in the activated synovial T cell population of patient 1012, as well as the other patients examined, likely results, not from random T cell trafficking, but from the selective expansion of those Vβ17-bearing T cells in the diseased tissue.

detectable in three of the five samples. Thus, T cells bearing these 3 Vβ polypeptides may also contribute to synovial inflammation.

TABLE 18

Analysis of IL-2R+ Synovial T Cells with Individual Vβ-specific Primers

| Patient # | Vβ Families | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 14 | 15 | 16 | 17 | 18 | 19 | 20 |
| 1012 | | | | + | + | | | | | | | | | | | + | | | |
| 1013 | | | | | | + | | | + | | | | + | | | + | | | |
| 1014 | | | | | | | | | | | + | | | | + | | | | |
| 1015 | | | + | | | + | + | + | + | | | + | + | + | | + | + | + | |
| 1020 | + | + | + | | + | | | | + | | | | + | + | | + | + | + | |

EXAMPLE XII

A. Detection of TCR β-Chain Transcripts in Synovial T Cells Using Vβ-Specific PCR-Amplification T cell receptor β-chain genes were amplified in two-stage reactions with individual Vβ-specific primers as described in Wucherfpennig et al., *Science*, 248:1016–1019 (1990), incorporated herein by reference, and nested Cβ primers. RNAs were reverse transcribed (1 hour, 42° C.) with the Cβext primer (40 pmol) in 12 μl of reaction buffer (Hart et al., supra). Reactions were diluted with a master mix (8 μl) containing nucleotides, reaction buffer minus $MgCl_2$ (final $Mg^{+2}$ concentration=3.6 mM) and Taq polymerase, apportioned among 19 tubes containing the individual Vβ primers. Samples were denatured (15 minutes, 95° C.) and 20 cycles of PCR were conducted. Each cycle consisted of a one minute denaturation at 95° C., a two minute annealing step and a two minute extension at 72° C. The first two cycles were annealed at 37° C. and 45° C. and the remainder at 50° C. One microliter aliquots of these Stage I reactions were added to 100 μl Stage II amplification reactions (Cetus Gene-Amp Kit) containing the Cβint primer (100 pmol) and 100 pmol of the Vβ primers used in the corresponding preamplifications. Stage II amplifications were conducted for 20 cycles with a 50° C. annealing temperature and without the 37° C. and 45° C. ramping. Five μl of each reaction was electrophoresed in 2% agarose gels, transferred to nitrocellulose and hybridized to a $^{32}$P-labeled β-chain constant region probe. Blots were exposed to X-ray film and scored for the presence or absence of Vβ-specific amplification.

B. Vβ17, Vβ14, Vβ9 and Vβ3 Transcripts are Common Among Activated Synovial T Cells To ensure that the prevalence of Vβ17 rearrangements in the earlier studies did not result from an amplification bias of the Vβ16mer primer, and to assess the presence of other Vβ genes in the synovium, TCR transcripts in the IL2-R+ samples were analyzed with a panel of 19 PCR primers, specific for known human Vβ gene families (Table 18). The Vβcons primer of Example XI is equivalent to the Vβ16mer primer. The number of Vβ genes detectable in these samples was variable, ranging from two to twelve. Vβ17 was found in four of the five patients, confirming the previous analyses using the Vβ16mer primer. Vβ14 transcripts also were found in four of the five patients and Vβ3 and Vβ9 transcripts were

EXAMPLE XIII

Vaccination Against EAE with a CDR4 Peptide of Vβ8.2

Rats were immunized with 100 pg of a synthetic peptide containing the sequence VPNGYKVSRPSQGDFFLTL (SEQ ID No.46) found in the fourth hypervariable or CDR4 region of the rat TCR β chain identified as Vβ8.2. The peptide, dissolved in saline, was emulsified in an equal volume of complete Freund's adjuvant (CFA) containing 10 mg/ul of mycobacterial tuberculosis. The animals were challenged 30 days later with 50 μg of guinea pig myelin basic protein in CFA. The CDR4 peptide vaccination resulted in a reduced incidence of disease as well as a reduced severity as measured both clinically and histologically as shown in Table 19. The histology was performed essentially as described in Hughes & Powell, *J. Neuropath. Exp. Neurol.* 43:154 (1984), which is incorporated herein by reference.

TABLE 19

Protection from EAE in the Rat by Vaccination with a TCR-DCR4 Peptide[1]

| Vaccination | Challenge | # Clinical Signs # Tested | Mean Max Severity[2] | Mean Onset | Mean Duration | # With Histology # Tested | Mean Histology Score[3] |
|---|---|---|---|---|---|---|---|
| Rat CDR4 in CFA | 50 μg MBP/ CFA | 6/10 | 1.5 | 11.8 | 5.4 | 3/10 | 0.6 |
| PBS/ CFA | 50 μg MBP/ CFA | 9/10 | 2.5 | 12.1 | 6.1 | 6/9 | 1.4 |
| None | 50 μg MBP/ CFA | 10/10 | 3.0 | 10.5 | 7.3 | 9/9 | 3.0 |

[1]rat CDR4 sequence: VPNGYKVSRPSQGDFFLTL (SEQ ID No. 46)
[2]graded on a 3-point scale as described in Example I
[3]graded on a 4-point scale Although the invention has been described with reference to the presently-preferred embodiment, it should be understood that various modifications can be made without departing from the spirit of the invention. Accordingly, the invention is limited only by the following claims.

We claim:

1. A method of preventing the proliferation of Vβ14-expressing T cells in a human individual having rheumatoid arthritis, comprising administering to said individual an effective amount of a cytotoxic or cytostatic agent, wherein said agent comprises an antibody, and wherein said antibody selectively binds Vβ14 expressed by said T cells.

2. A method of preventing the proliferation of Vβ17-expressing T cells in a human individual having rheumatoid arthritis, comprising administering to said individual an effective amount of a cytotoxic or cytostatic agent, wherein said agent comprises an antibody, and wherein said antibody selectively binds Vβ17 expressed by said T cells.

3. The method of claim 1, wherein said antibody is attached to a moiety selected from the group consisting of radioactive moieties and chemotherapeutic moieties.

4. The method of claim 2, wherein said antibody is attached to a moiety selected from the group consisting of radioactive moieties and chemotherapeutic moieties.

* * * * *

UNITED STATES PATENT AND TRADEMARK OFFICE
CERTIFICATE OF CORRECTION

PATENT NO. : 6,221,352 B1
DATED : April 24, 2001
INVENTOR(S) : Howell et al.

It is certified that error appears in the above-identified patent and that said Letters Patent is hereby corrected as shown below:

Title page,
Item [62], please delete "Jul. 18, 1999," and replace with -- Jul. 18, 1989, --.

OTHER PUBLICATIONS, please delete "mediatinng" and replace with -- mediating --; please delete "lymphocite" and replace with -- lymphocyte --.

ABSTRACT,
Line 10, please delete "completed" and replace with -- complexed --.

Column 1,
Line 15, please delete "1989. Now abandoned the contents" and replace with -- 1989, now abandoned. The contents --.

Column 3,
Line 13, please delete "effect" and replace with -- affect --.
Line 53, please delete "is effectively" and replace with -- effectively --.

Column 7,
Line 15, please delete
"MGIRLLCRAVAFCFIAVGLVDVKVTQSSEYLCKERFWKCDLWXCSMSHWNM DQYEUSPFLFLELIYDAYSCKMKWKFSIPEGYSVSREKKERFSLILESASTNQTS MYLCASS" and replace with --
MGIRLLCRVAFCFLAVGLVDVKVTQSSRYLVKRTGEKVFLECVQDMDHENMF WYRQDPGLGLRLIYFSYDVKMKEKGDIPEGYSVSREKKERFSLILESASTNQTS MYLCASS --.
Line 22, please delete "IPEGYSVSREKKERFSLILESASTNQTTSMYLCASS (SEQ ID NO:10)." and replace with -- IPEGYSVSREKKERFSLILESASTNQTSMYLCASS (SEQ ID NO:10). --.
Line 43, please delete "BVDJ" and replace with -- βVDJ --.

Column 8,
Line 1, please delete "TCRS." and replace with -- TCRs. --.

Column 10,
Line 41, Table 2, please delete "hVBβ3" and replace with -- hVβ3 --.
Line 51, Table 2, please delete "KGYRVSRKREHFSL" and replace with -- KGYRVSRKKREHFSL --.

UNITED STATES PATENT AND TRADEMARK OFFICE
CERTIFICATE OF CORRECTION

PATENT NO. : 6,221,352 B1
DATED : April 24, 2001
INVENTOR(S) : Howell et al.

It is certified that error appears in the above-identified patent and that said Letters Patent is hereby corrected as shown below:

Column 11,
Line 3, please delete "V62 8.2a," and replace with -- Vβ8.2a, --.

Column 12,
Line 17, please delete "TCRS," and replace with -- TCRs, --.

Column 15,
Line 56, please delete "VW" and replace with -- VDJ --.

Column 16,
Line 36, please delete "VW" and replace with -- VDJ --.
Line 40, please delete "BLO.PL" and replace with -- B10.PL --.

Column 17,
Line 66, please delete "IPA" and replace with -- IFA --.

Column 18,
Line 40, Table 8, second column, please delete "6/16" and replace with -- 6/10 --;
Line 66, please delete "J a" and replace with -- Jα --.

Column 19,
Line 24, please delete "J α" and replace with -- Jα --.
Line 33, please delete "J$_\alpha$TA39" and replace with -- JαTA39 --.
Line 63, please delete "VW" and replace with -- VDJ --.

Column 21,
Line 5, Table 11, please delete "J52.1" and replace with -- Jβ2.1 --.

Column 22,
Line 54, please delete "(n-256)" with -- (n=256) --.
Line 62, please delete "Priori" and replace with -- priori --.

Column 24,
Line 25, please delete "Vβsequence," and replace with -- Vβ sequence, --.
Line 58, Table 14, please move the "1.2" under the "SEQ ID NO." column to read -- Jβ1.2 --.
Line 62, Table 14, please move the "2.7" under the "SEQ ID NO." column to read -- Jβ2.7 --.

UNITED STATES PATENT AND TRADEMARK OFFICE
CERTIFICATE OF CORRECTION

PATENT NO. : 6,221,352 B1
DATED : April 24, 2001
INVENTOR(S) : Howell et al.

It is certified that error appears in the above-identified patent and that said Letters Patent is hereby corrected as shown below:

Column 27,
Table 16, please move the "3" out of the "SEQ ID NO." column.
Table 16, please delete the following

A

"5' G T A G T T G T T C T G C A 3'"

G and replace with the following:

A

-- 5' G T A G T T G T T C T G C A 3' --

G

Column 29,
Line 26, please delete "described Stedman" and replace with -- described in Stedman --.

Column 34,
Line 27, please delete "100 pg" and replace with -- 100 µg --.

Signed and Sealed this

Thirtieth Day of April, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:1:

Ser Gly Asp Gln Gly Gly Asn Glu
1               5

(2) INFORMATION FOR SEQ ID NO:2:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:2:

Cys Ala Ile Gly Ser Asn Thr Glu
1               5

(2) INFORMATION FOR SEQ ID NO:3:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:3:

Ala Ser Ser Leu Gly Gly Ala Val Ser Tyr Asn
1               5                   10

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:4:

Ala Ser Ser Leu Gly Gly Glu Glu Thr Gln Tyr Phe
1               5                   10

(2) INFORMATION FOR SEQ ID NO:5:

(i) SEQUENCE CHARACTERISTICS:

(A) LENGTH: 12 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:5:

Ala Ser Ser Leu Gly Gly Phe Glu Thr Gln Tyr Phe
1               5                   10

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:6:

Ala Ser Ser Leu Gly Gly Thr Glu Ala Phe Phe
1               5                   10

(2) INFORMATION FOR SEQ ID NO:7:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:7:

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser (2) INFORMATION FOR SEQ ID NO:8:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:8:

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65              70                  75                      80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Ser
```

(2) INFORMATION FOR SEQ ID NO:9:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:9:

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65              70                  75                      80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser
```

(2) INFORMATION FOR SEQ ID NO:10:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:10:

```
Met Gly Ile Arg Leu Leu Cys Arg Val Ala Phe Cys Phe Leu Ala Val
1               5                   10                  15
```

```
Gly Leu Val Asp Val Lys Val Thr Gln Ser Ser Arg Tyr Leu Val Lys
                20                  25                  30

Arg Thr Gly Glu Lys Val Phe Leu Glu Cys Val Asp Met Asp His Glu
            35                  40                  45

Asn Met Phe Trp Tyr Gln Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser
```

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:11:

```
Glu Gly Tyr Ser Val Ser Arg Glu Lys Lys Glu Ser Phe Pro Leu
1               5                   10                  15
```

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:12:

```
Glu Gly Tyr Ser Val Ser Arg Glu Lys Lys Glu Arg Phe Ser Leu
1               5                   10                  15
```

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:13:

```
Glu Gly Tyr Lys Val Ser Arg Lys Glu Lys Arg Asn Phe Pro Leu
1               5                   10                  15
```

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:14:

Asp Gly Tyr Ser Val Ser Arg Ser Lys Thr Glu Asp Phe Leu Leu
1               5                  10                  15

(2) INFORMATION FOR SEQ ID NO:15:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:15:

Asn Arg Phe Ser Pro Lys Ser Pro Asp Lys Ala His Leu Asn Leu
1               5                  10                  15

(2) INFORMATION FOR SEQ ID NO:16:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:16:

Glu Gly Tyr Asp Ala Ser Arg Glu Lys Lys Ser Ser Phe Ser Leu
1               5                  10                  15

(2) INFORMATION FOR SEQ ID NO:17:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:17:

Lys Gly Tyr Arg Val Ser Arg Lys Lys Arg Glu His Phe Ser Leu
1               5                  10                  15

(2) INFORMATION FOR SEQ ID NO:18:

(i) SEQUENCE CHARACTERISTICS:
         (A) LENGTH: 15 amino acids
         (B) TYPE: amino acid
         (D) TOPOLOGY: linear (ii) MOLECULE TYPE: peptide (v) FRAGMENT TYPE: N-terminal (xi) SEQUENCE DESCRIPTION: SEQ ID NO:18:

Asp Gly Tyr Lys Ala Ser Arg Pro Ser Gln Glu Asn Phe Ser Leu
1               5                  10                  15

(2) INFORMATION FOR SEQ ID NO:19:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:19:

Asp Gly Tyr Lys Ala Ser Arg Pro Ser Gln Lys Glu Phe Ser Leu
1               5                  10                  15

(2) INFORMATION FOR SEQ ID NO:20:

(i) SEQUENCE CHARACTERISTICS:
      (A) LENGTH: 18 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:20:

Asp Gly Tyr Asn Val Ser Arg Leu Lys Lys Gln Asn Phe Leu Leu Gly
1               5                  10                  15

Leu Glu (2) INFORMATION FOR SEQ ID NO:21:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:21:

Ser Ser Asp Ser Ser Asn Thr Glu
1               5

(2) INFORMATION FOR SEQ ID NO:22:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:22:

Ser Ser Asp Ser Gly Asn Thr Glu
1               5

(2) INFORMATION FOR SEQ ID NO:23:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (v) FRAGMENT TYPE: N-terminal (xi) SEQUENCE DESCRIPTION: SEQ ID NO:23:

Ser Gly Asp Ala Gly Gly Gly Tyr Glu
1               5

(2) INFORMATION FOR SEQ ID NO:24:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:24:

Ser Ser Asp Ser Ser Asn Thr Glu
1               5

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:25:

Cys Ala Ser Ser Asp Ser Ser Asn Thr Glu Val Phe Phe Gly Lys
1               5                   10                  15

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:26:

Cys Ala Ser Ser Asp Ser Gly Asn Thr Glu Val Phe Phe Gly Lys
1               5                   10                  15

(2) INFORMATION FOR SEQ ID NO:27:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:27:

Cys Ala Ser Ser Asp Ser Gly Asn Val Leu Tyr Phe Gly Glu Gly Ser
1               5                   10                  15
Arg (2) INFORMATION FOR SEQ ID NO:28:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:28:

Ala Ser Ser Asp Ser Ser Asn Thr Glu
1               5

(2) INFORMATION FOR SEQ ID NO:29:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:29:

Asp Met Gly His Gly Leu Arg Leu Ile His Tyr Ser Tyr Asp Val Asn
1               5                   10                  15

Ser Thr Glu Lys
            20

(2) INFORMATION FOR SEQ ID NO:30:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:30:

Asp Met Gly His Gly Leu Arg Leu Ile His Tyr Ser Tyr Asp Val Asn
1               5                   10                  15

Ser Thr Glu Lys Gly
            20

(2) INFORMATION FOR SEQ ID NO:31:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:31:

Arg Phe Gly Ala Gly Thr Arg Leu Thr Val Lys
1               5                   10

(2) INFORMATION FOR SEQ ID NO:32:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

CTCTGCAGCG GAGACCAGGG CGGCAATGAG CAGTTCTTC                                        39

(2) INFORMATION FOR SEQ ID NO:33:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:33:

Ser Gly Asp Gln Gly Gly Asn Glu Gln Phe Phe
1               5                   10

(2) INFORMATION FOR SEQ ID NO:34:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

GGAGACAGGA GGAAAGA                                                                17

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

GGCGACCAAG GCGGCAACGA A                                                           21

(2) INFORMATION FOR SEQ ID NO:36:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

GGGGATCAGG GGGGGAATGA G                                                           21

(2) INFORMATION FOR SEQ ID NO:37:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

GGTGACAGGT GGTAAGA                                                    17

(2) INFORMATION FOR SEQ ID NO:38:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:38:

Tyr Leu Cys Ala Ser Lys Asn Pro Thr Val Ser Tyr Gly Tyr Thr Phe
1               5                   10                  15

(2) INFORMATION FOR SEQ ID NO:39:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TATCTCTGTG CCAGTAAAAA TCCCACGGTC TCCTATGGCT ACACCTTC                  48

(2) INFORMATION FOR SEQ ID NO:40:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:40:

Tyr Leu Cys Ala Ser Asp Asn Glu Ser Phe Phe Gly Gln Gly
1               5                   10

(2) INFORMATION FOR SEQ ID NO:41:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TATCTCTGTG CCAGTGACAA CGAGAGTTTC TTTGGACAAG GC                        42

(2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:42:

Tyr Leu Cys Ala Ser Val Arg Asp Arg Arg Asn Tyr Gly Tyr Thr
1               5                   10                  15

(2) INFORMATION FOR SEQ ID NO:43:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

TATCTCTGTG CCAGTGTGAG GGACAGGAGA AACTATGGCT ACACC                45

(2) INFORMATION FOR SEQ ID NO:44:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:44:

Tyr Leu Cys Ala Ser Ser Ser Ile Asp Ser Ser Tyr Glu Gln Tyr
1               5                   10                  15

(2) INFORMATION FOR SEQ ID NO:45:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

TATCTCTGTG CCAGTAGTAG TATAGACTCC TCCTACGAGC AGTAC                45

(2) INFORMATION FOR SEQ ID NO:46:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:46:

Val Pro Asn Gly Tyr Lys Val Ser Arg Pro Ser Gln Gly Asp Phe Phe
1               5                   10                  15

Leu Thr Leu (2) INFORMATION FOR SEQ ID NO:47:

(i) SEQUENCE CHARACTERISTICS:
            (A) LENGTH: 16 base pairs
            (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:47:

TGTACTGGTA CAAACA                                                   16

(2) INFORMATION FOR SEQ ID NO:48:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:48:

TTTTTTGGTA TCGTCA                                                   16

(2) INFORMATION FOR SEQ ID NO:49:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:49:

TCACAGATAG TAAATGACTT TCAG                                          24

(2) INFORMATION FOR SEQ ID NO:50:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:50:

TCTCCACTCT GAAGATCC                                                 18

(2) INFORMATION FOR SEQ ID NO:51:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:51:

GATTTCCTCC TCACTCTG                                                 18

(2) INFORMATION FOR SEQ ID NO:52:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:52:

CAAGCTGTTC CCACCCGA                    18

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CCAGAAGGTG GCCGAGAC                    18

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

GCGGCTGCTC AGGCAGTA                    18

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

CGACCTCGGG TGGGAACA                    18

(2) INFORMATION FOR SEQ ID NO:56:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GAAGTCTGGA ACAGC                       15

(2) INFORMATION FOR SEQ ID NO:57:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

GACGTCTGGA ACAGC                       15

(2) INFORMATION FOR SEQ ID NO:58:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

GTAGTATGTT CTGCA                                                    15

(2) INFORMATION FOR SEQ ID NO:59:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

GTAGTGTGTT CTGCA                                                    15

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

CTCCTCGAGC AGAGGCGGGC CGCG                                          24

(2) INFORMATION FOR SEQ ID NO:61:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

TTCCTCGAGG ACAGGCGCGC CGCG                                          24

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

CTCCTCGAGC AGAAGCGGGG CCGG                                          24

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

CTCCTCGAGC AGAAGCGGGC CGCG                                              24

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CTCCTCGAGC AGAGGCGGGC CGAG                                              24

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

ATCCTCGAAG ACGAGCGGGC CGCG                                              24

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

ATCCTCGAGG ACAGGCGGGG CCAG                                              24

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

TTCCTCGAAG ACAGGCGGGC CCTG                                              24

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:68:

TTCCTCGAGC GGAGGCGGGC CGAG                                              24

(2) INFORMATION FOR SEQ ID NO:69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

ATCCTCGAGC AGGCGCGGGC CGCG                                              24

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

CTCCTCGAGC AGAAGCGGGG CCAG                                              24

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

CTCCTCGAGC GGAGGCGGGC CGAG                                              24

(2) INFORMATION FOR SEQ ID NO:72:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO:72:

Asp Pro Gly Leu Gly Leu Arg Leu Ile Tyr Phe Ser Tyr Asp Val Lys
1               5                   10                  15

Met Lys Glu Lys Gly
            20

(2) INFORMATION FOR SEQ ID NO:73:

(i) SEQUENCE CHARACTERISTICS:
        (A) LENGTH: 21 amino acids
        (B) TYPE: amino acid (D) TOPOLOGY: linear (ii) MOLECULE TYPE: peptide (v) FRAGMENT TYPE: N-terminal (xi) SEQUENCE DESCRIPTION: SEQ ID NO:73:

Asp Pro Gly Leu Gly Leu Arg Gln Ile Tyr Tyr Ser Met Asn Val Glu
1               5                  10                  15

Val Thr Asp Lys Gly
            20

(2) INFORMATION FOR SEQ ID NO:74:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:74:

Asp Pro Gly Gln Gly Leu Arg Leu Ile Tyr Tyr Ser Gln Ile Val Asn
1               5                  10                  15

Lys Phe Gln Lys Gly
            20

(2) INFORMATION FOR SEQ ID NO:75:

(i) SEQUENCE CHARACTERISTICS:
            (A) LENGTH: 101 amino acids
            (B) TYPE: amino acid
            (D) TOPOLOGY: linear (ii) MOLECULE TYPE: peptide (v) FRAGMENT TYPE: N-terminal (xi) SEQUENCE DESCRIPTION: SEQ ID NO:75:

Phe Leu Ala Val Gly Leu Val Asp Val Lys Val Thr Gln Ser Ser Arg
1               5                  10                  15

Tyr Leu Val Lys Arg Thr Gly Glu Lys Val Phe Leu Glu Cys Val Gln
                20                  25                  30

Asp Met Asp His Glu Asn Met Phe Trp Tyr Arg Gln Asp Pro Gly Leu
            35                  40                  45

Gly Leu Arg Leu Ile Tyr Phe Ser Tyr Asp Val Lys Met Lys Glu Lys
        50                  55                  60

Gly Asp Ile Pro Glu Gly Tyr Ser Val Ser Arg Glu Lys Lys Glu Arg
65                  70                  75                  80

Phe Ser Leu Ile Leu Glu Ser Ala Ser Thr Asn Gln Thr Ser Met Tyr
                85                  90                  95

Leu Cys Ala Ser Ser
            100